United States Patent
Lim et al.

(10) Patent No.: US 10,842,442 B2
(45) Date of Patent: Nov. 24, 2020

(54) ELECTRONIC APPARATUS AND CONTROL METHOD THEREOF

(71) Applicant: SAMSUNG ELECTRONICS CO., LTD., Suwon-si (KR)

(72) Inventors: Hyung-joon Lim, Seoul (KR); Hwan Shim, Suwon-si (KR); Young-hwan Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 946 days.

(21) Appl. No.: 15/368,857

(22) Filed: Dec. 5, 2016

(65) Prior Publication Data
US 2017/0156678 A1    Jun. 8, 2017

(30) Foreign Application Priority Data

Dec. 7, 2015  (KR) .................. 10-2015-0173169
Oct. 24, 2016  (KR) .................. 10-2016-0138712

(51) Int. Cl.
*A61B 5/00* (2006.01)
*A61B 7/04* (2006.01)
(Continued)

(52) U.S. Cl.
CPC ........ *A61B 5/7232* (2013.01); *A61B 5/04012* (2013.01); *A61B 7/04* (2013.01);
(Continued)

(58) Field of Classification Search
CPC ... A61B 5/7232; A61B 5/04012; A61B 5/742; A61B 5/02416; A61B 5/0402; A61B 7/04
See application file for complete search history.

(56) References Cited

U.S. PATENT DOCUMENTS 4,947,858 A * 8/1990 Smith .................. A61B 5/0006
                                                              600/509
5,623,935 A * 4/1997 Faisandier ......... A61B 5/04325
                                                              600/509
(Continued)

FOREIGN PATENT DOCUMENTS

KR    10-2014-0104143    8/2014

OTHER PUBLICATIONS

Korean Office Action dated May 18, 2018 issued in Korean Patent Application No. 10-2016-0138712 and English translation, 16 pp.
(Continued)

*Primary Examiner* — Peter Luong
(74) *Attorney, Agent, or Firm* — Nixon & Vanderhye P.C.

(57) ABSTRACT

Disclosed is an electronic apparatus for measuring a biometric signal, the electronic apparatus including: a measurer comprising measuring circuitry configured to measure a biometric signal of a person to be examined, and to generate a measured signal having a waveform corresponding to a characteristic of the biometric signal; a signal processor configured to process the generated measured signal; and a controller configured to control the signal processor to generate a compressed signal by compressing the measured signal and at least one piece of characteristic information included in a waveform of the measured signal, when the measured signal is compressed. Thus, a measured biometric signal is efficiently compressed while reducing a loss of main characteristic information.

20 Claims, 22 Drawing Sheets

(51) Int. Cl.
  *A61B 5/04* (2006.01)
  *A61B 5/0402* (2006.01)
  *A61B 5/024* (2006.01)

(52) U.S. Cl.
  CPC ......... *A61B 5/02416* (2013.01); *A61B 5/0402* (2013.01); *A61B 5/742* (2013.01)

(56) References Cited

U.S. PATENT DOCUMENTS

| | | |
|---|---|---|
| 2008/0177789 A1 | 7/2008 | Stoval |
| 2012/0014575 A1* | 1/2012 | Wang .................... H04N 19/63 382/128 |
| 2012/0257698 A1 | 10/2012 | Zhang |
| 2012/0323131 A1 | 12/2012 | Ting et al. |
| 2013/0013333 A1 | 1/2013 | Gopinathan et al. |
| 2013/0090567 A1 | 4/2013 | Lee et al. |
| 2013/0289424 A1 | 10/2013 | Brockway et al. |
| 2014/0243693 A1 | 8/2014 | Koyama et al. |
| 2015/0005655 A1 | 1/2015 | Sato |

OTHER PUBLICATIONS

Extended Search Report dated Aug. 29, 2018 in counterpart EuropeanPatent Application No. 16873291.5.

Zou,Yao et al, "An Energy-Efficient Design for ECG Recording and R-Peak Detection Based on Wavelet Transform," IEEE Transactions on Circuiits and Systems II: Express Briefs, IEEE, US,vol. 62, No. 2, Feb. 1, 2015, pp. 119-123, XP011572733,ISSN: 1549-7747, DOI: 10.1109/TCSII.2014.2368619 [retrieved on Feb. 6, 2015].

Cardenas-Barrera, Julian L. et al, "Mean-Shape Vector Quantizer for ECG Signal Compression," IEEE Transactions on Biomedical Engineering, IEEE Service Center, Piscataway, NJ, USA, vol. 46, No. 1, Jan. 1, 1999, XP011006639,ISSN: 0018-9294.

Search Report and Written Opinion dated Mar. 20, 2017 in counterpart International Patent Application No. PCT/KR2016/014080.

* cited by examiner

FIG. 9
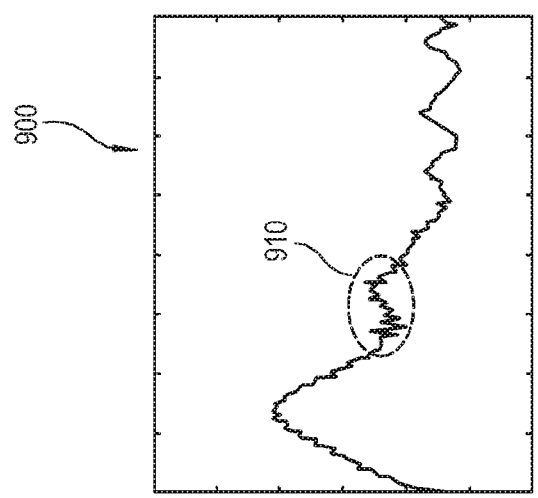
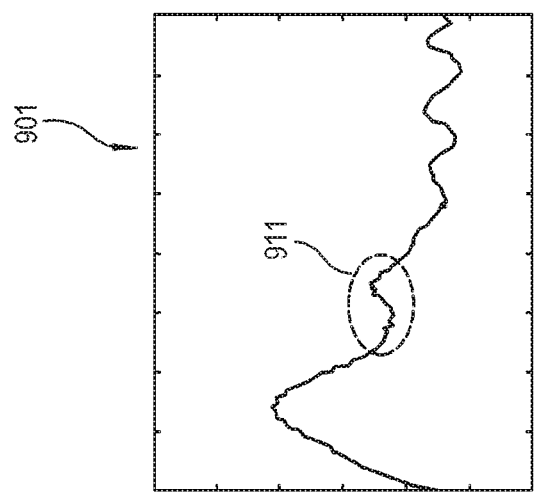
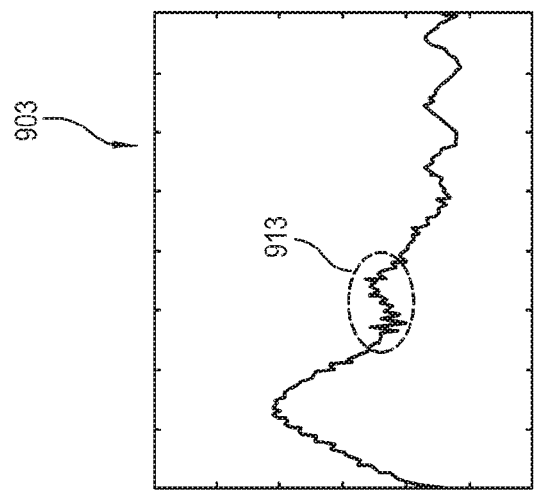

ELECTRONIC APPARATUS AND CONTROL METHOD THEREOF

CROSS-REFERENCE TO RELATED APPLICATIONS

This application is based on and claims priority under 35 U.S.C. § 119 to Korean Patent Application No. 10-2015-0173169, filed on Dec. 7, 2015 in the Korean Intellectual Property Office and Korean Patent Application No. 10-2016-0138712, filed on Oct. 24, 2016 in the Korean Intellectual Property Office, the disclosures of which are incorporated by reference herein in their entireties.

BACKGROUND

Field

The present disclosure relates generally to an electronic apparatus for measuring a body signal of a patient, and for example, to an electronic apparatus which measures a body signal of a person to be examined, and efficiently compresses the measured signal to be stored or sent.

Description of Related Art

With a development in science, medical technology has also continued to develop. Accordingly, health care service has been offered in various fields to promote health, and developed to prevent and administer diseases by monitoring a user's biometric information, health information, etc. Further, appearance of wearable devices for the health care introduces various sensors for measuring a biometric signal, and enables early diagnosis of diseases, thereby increasing interest in utilizing the biometric signal. In addition, the introduction of various sensors for the biometric signal rapidly increases the amount of health/medical data, and thus such a vast amount of data is required to be efficiently compressed, stored and sent.

To use a biometric signal for the early diagnosis of diseases, there has been growing interest in a method of measuring an electrocardio graph (ECG), a photoplethsymo graph (PPG), a phonocardio graph (PCG) and the like biometric signal and utilizing the measured biometric signal to the outside for utilization. As the amount of data increases, interest in a method of efficiently compressing the measured biometric signal has also been on the rise. The method of compressing a signal is classified into a lossless compression method, a lossy compression method, etc. If a signal is compressed by the lossless compression method, main information of the signal is not lost, but a compression efficiency is lower than that of the lossy compression method. The lossy compression method is based on energy of a signal, and removes unnecessary data having low energy to thereby raise the compression efficiency. Therefore, if the measured biometric signal is compressed by the lossy compression method in order to increase the efficiency of storing data, some main information may be lost when the compressed data is decompressed, and thus the decompressed biometric signal may be not equal to the original biometric signal measured before the compression. Accordingly, there is a problem that the main information related to points of a medical diagnostic subject is lost.

SUMMARY

An example aspect of one or more example embodiments may provide an electronic apparatus and a control method thereof, in which a measured biometric signal is more efficiently compressed without losing main characteristic information.

According to an aspect of an example embodiment, an electronic apparatus for measuring a biometric signal is provided, the electronic apparatus including: a measurer comprising biometric signal measuring circuitry configured to measure a biometric signal of a person to be examined, and to generate a measured signal having a waveform corresponding to a characteristic of the biometric signal; a signal processor configured to process the generated measured signal; and a controller configured to control the signal processor to generate a compressed signal by compressing the measured signal and at least one piece of characteristic information included in a waveform of the measured signal, when the measured signal is compressed.

The controller may control the signal processor to decompress the compressed signal so that at least a part of the compressed signal, which is lost by compression, can be recovered based on the characteristic information, when the compressed signal is decompressed. Thus, efficient compression and decompression are possible.

The measured signal may include a plurality of periods, and the controller may control the signal processor to generate a plurality of one-period signals by extracting a signal having one-period from the measured signal corresponding to each period of the measured signal, to generate the compressed signal by compressing each one-period signal, and to generate at least one piece of characteristic information included in each one-period signal. Thus, a process of compressing the measured signal is introduced.

The biometric signal may include at least one among an electrocardio graph (ECG), a photoplethsymo graph (PPG), and a phonocardio graph (PCG). Thus, it is possible to measure, compress and decompress various kinds of biometric signal.

The controller may control the signal processor to generate characteristic information related to at least one medical diagnosis point included in the waveform of the measured signal, and the medical diagnosis point may include at least one of time of when a plurality of peaks occurs in the waveform, an amplitude of each peak, intervals between the peaks, difference in amplitude between the peaks, a period of the waveform, a position of a heart murmur in the waveform, and a level of the heart murmur. Thus, it is possible to consider various pieces of characteristic information of the biometric signal.

The electronic apparatus may further include a storage configured to store health information and the controller may analyze the characteristic information based on the health information and generate diagnostic information of a person to be examined. Thus, it is convenient for a user to take a simple examination without going to a hospital.

The electronic apparatus may further include various output circuitry configured to output at least one of the diagnostic information, the characteristic information and the decompressed signal. Thus, it is possible to provide information to a user.

The output circuitry may include a display to display an image based on at least one of the diagnostic information, the characteristic information and the decompressed signal. Thus, it is possible to provide visual information to a user.

The output circuitry may include a loudspeaker to make a voice or sound based on at least one of the diagnostic information, the characteristic information and the decompressed signal. Thus, it is possible to provide acoustic information to a user.

The controller may change the characteristic information based on a selection, and decompress the compressed signal based on the changed characteristic information. Thus, the characteristic information is variously changeable, or the compressed signal is decompressed in accordance with the changed characteristic information, thereby giving improved usability to a user.

The controller may generate a decompressed signal by decompressing the compressed signal, compare the characteristic information and the decompressed signal, determine a difference between the decompressed signal and the characteristic information as a loss, and restore the loss based on the characteristic information to thereby decompress the compressed signal. Thus, the signal having a loss due to compression is decompressed based on the characteristic information, and thus efficient compression and decompression are possible.

The controller may control the signal processor to generate the characteristic information from the measured signal based on the kind of biometric signal determined based on a selection. Thus, it is more convenient for a user.

According to another aspect of an example embodiment, a method of controlling an electronic apparatus for measuring a biometric signal is provided, the method including: generating a measured signal having a waveform corresponding to a characteristic of the biometric signal by measuring the biometric signal of a person to be examined; and compressing the measured signal and characteristic information related to at least one medical diagnosis point included in the waveform of the measured signal to generate a compressed signal.

The method of controlling an electronic apparatus may further include decompressing the compressed signal so that at least a part of the compressed signal, which is lost by compression, can be recovered based on the characteristic information. Thus, a process of more efficiently compressing and decompressing the measured signal is introduced.

The measured signal may include a plurality of periods, and the compressing the measured signal may include: generating a plurality of one-period signals by extracting a signal having one-period from the measured signal to correspond to each period of the measured signal; and generating the compressed signal by compressing each one-period signal, and generating at least one piece of characteristic information included in each one-period signal. Thus, a process of compressing the measured signal is introduced.

The biometric signal may include at least one among an electrocardio graph (ECG), a photoplethsymo graph (PPG), and a phonocardio graph (PCG). Thus, it is possible to measure, compress and decompress various kinds of biometric signal. In this example embodiment, the biometric signal may include brainwaves, blood pressure, a bloodstream, blood sugar, a body temperature, oxygen saturation, skin resistance, an electromyogram (EMG), or a pupillary motion.

The compressing the measured signal may include: controlling the signal processor to generate characteristic information related to at least one medical diagnosis point included in the waveform of the measured signal, and the medical diagnosis point may include at least one among time of when a plurality of peaks occurs in the waveform, an amplitude of each peak, intervals between the peaks, difference in amplitude between the peaks, a period of the waveform, a position of a heart murmur in the waveform, and a level of the heart murmur. Thus, it is possible to consider various pieces of characteristic information of the biometric signal.

The method of controlling an electronic apparatus may further include: storing health information; and analyzing the characteristic information based on the health information and generating diagnostic information of a person to be examined. Thus, it is convenient for a user to take a simple examination without going to a hospital.

The method of controlling an electronic apparatus may further include outputting at least one of the health information, the diagnostic information, and the decompressed signal. Thus, it is possible to provide information to a user.

The decompressing the compressed signal may include: changing the characteristic information based on a selection; and decompressing the compressed signal based on the changed characteristic information. Thus, the characteristic information is variously changeable, or the compressed signal is decompressed in accordance with the changed characteristic information, thereby giving improved usability to a user.

BRIEF DESCRIPTION OF THE DRAWINGS

The above and/or other aspects will become apparent and more readily appreciated from the following detailed description, taken in conjunction with the accompanying drawings, in which like reference numerals refer to like elements, and wherein:

FIG. 9 is a diagram illustrating example compression and decompression of a phonocardio graph according to an example embodiment;

DETAILED DESCRIPTION

Figure 1:
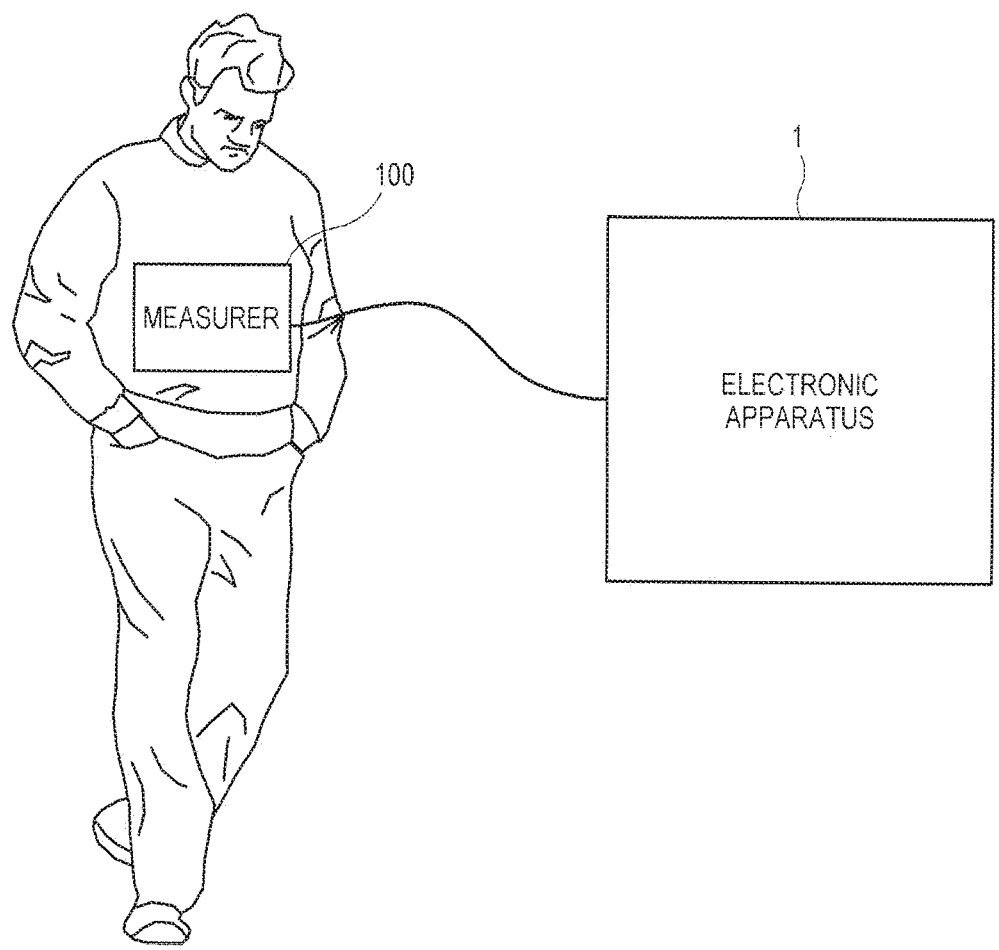
FIG. 1 is a diagram illustrating an example of using an electronic apparatus according to an example embodiment.

Below, example embodiments will be described in greater detail with reference to accompanying drawings so as to be easily realized by a person having an ordinary skill in the art. The present disclosure may be embodied in many different forms, and not limited to the following example embodiments. Portions unrelated to the descriptions may be omitted for clarity, and like numerals refer to like elements throughout.

In this disclosure, an electronic apparatus may refer, for example, to an apparatus for measuring a biometric signal of a person to be examined. According to an example embodiment, the electronic apparatus may be configured to measure a biometric signal of a person to be examined, store and compress characteristic information of the measured signal, and decompress the compressed signal so that a medical diagnostic service can be provided to the person to be examined.

Further, in this disclosure, a person to be examined may refer, for example, to a user of the electronic apparatus according to an example embodiment. The electronic apparatus may be configured to measure a biometric signal of the person to be examined. For example, the electronic apparatus may be configured to measure the biometric signal of the person to be examined for the purpose of medical diagnosis.

Further, in this disclosure, the biometric signal may refer, for example, to a signal or voltage level generated according to repetitive motions inside a body of a person to be examined and measured from a surface of the body of the person to be examined, in which the signal has a plurality of periods corresponding to the motions of the body.

Further, in this disclosure, the measured signal may refer, for example, to a signal having a waveform, which is generated based on the measured biometric signal and has a plurality of periods since it is generated corresponding to the characteristic of the biometric signal.

Further, in this disclosure, the characteristic information may refer, for example, to information involved in the waveform of the measured signal. For example, the characteristic information is generated at least one point of the waveform of the measured signal and used for a medical diagnosis.

Further, in this disclosure, a compressed signal may refer, for example, to a signal generated by compressing the measured signal. The compression may be achieved by various methods such as a method of removing coefficients based on a specific compression method, a method of dividing the measured signal having a plurality of periods into respective one-period signals and applying a previously stored analogous template to each of the one-period signals, etc. However, it is not required to extract the one-period signal from the measured signal. A signal having a plurality of periods, each of which is shorter than the period of the measured signal, may be extracted from the measured signal, and the characteristic information may be generated from this extracted signal and then compressed.

Figure 21:
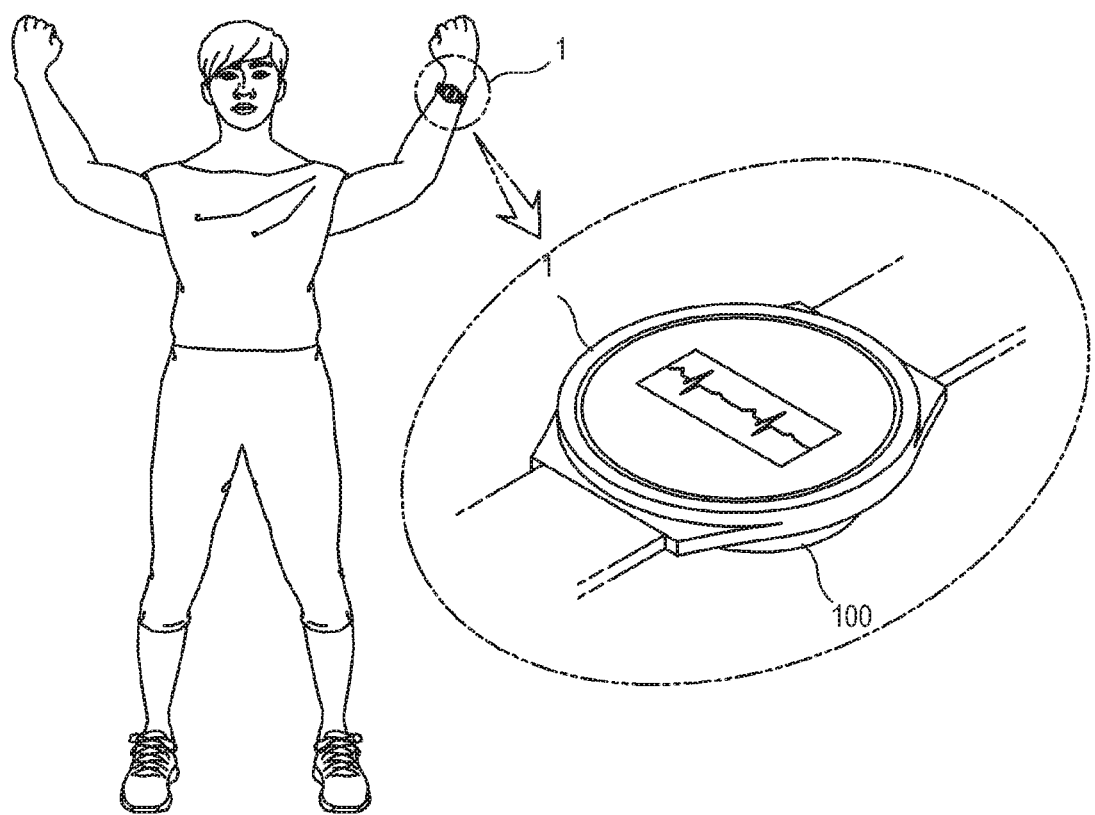
FIG. 21 is a diagram illustrating an example of the electronic apparatus according to an example embodiment.
Figure 22:
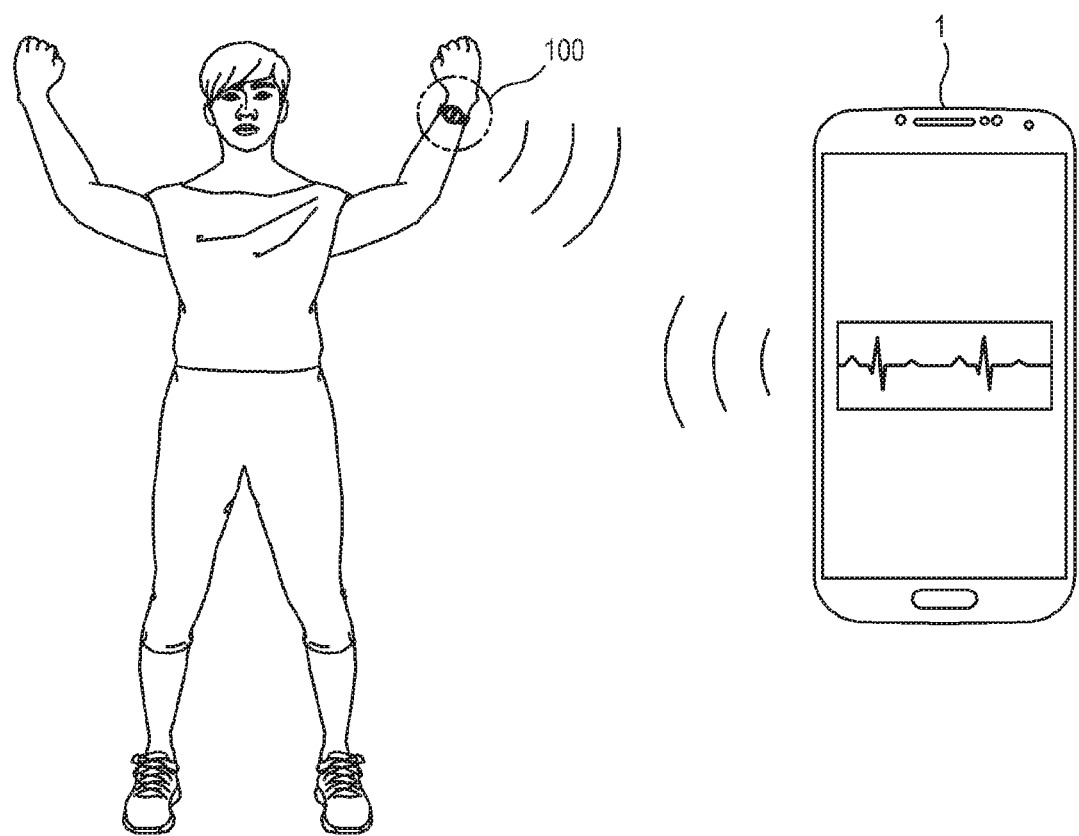
FIG. 22 is a diagram illustrating an example of the electronic apparatus according to an example embodiment.

Further, in this disclosure, the decompressed signal may refer, for example, to a signal generated by decompressing the compressed signal. The decompression may be carried out based on the compression method. The compressed signal may include information about the compression method. If the compression is performed using the previously stored template, the characteristic information lost by the compression may be restored to thereby decompress the compressed signal. FIG. 1, FIG. 21 and FIG. 22 are diagrams illustrating an example electronic apparatus according to an example embodiment, which measures, compress and stores a biometric signal of a person to be examined. The biometric signal may refer, for example, to a signal obtained by measuring a voltage level, a sound, a pulsation or the like, which is generated corresponding to a repetitive biometric motion inside a body of a living thing, on a surface of a body through a sensor, a sensor, a microphone, etc. For example, the biometric signal includes an electrocardio graph (ECG) obtained by measuring a voltage level related to a heartbeat, a phonocardio graph (PCG) obtained by measuring sound of a heartbeat, a photoplethsymo graph (PPG) showing pulsations of arteries and veins based on motions of a heart, etc. Such a biometric signal is generated based on repetitive motions, and thus has periodicity.

The electronic apparatus 1 includes a measurer (e.g., including measuring circuitry) 100, which is attached to a body part of a person to be examined and which may measure, for example, the electrocardio graph (ECG), the photoplethsymo graph (PPG), the phonocardio graph (PCG) or the like biometric signal having the periodicity, and compresses the measured signal. The electronic apparatus 1 is configured to extract at least characteristic information of a waveform from the measured signal while compressing the measured signal. The electronic apparatus 1 is configured to store the extracted characteristic information and the compressed signal, and provide the extracted characteristic information and the compressed signal as diagnostic information in accordance with a user's selection.

For example, the characteristic information is extracted and generated at a point for medical diagnosis, which is included in the waveform of the measured signal. For example, specific points in the waveform are used for the medical diagnosis based on the measured signal, and the characteristic information includes information at the specific points. In this disclosure, the characteristic information may refer, for example, to at least one piece of information included in the measured signal having an electric waveform. For example, if the biometric signal is the electrocardio graph, the characteristic information may include various points of the electrocardio graph used in the medical diagnosis, such as time of each of peaks P, Q, R, S and T of the electrocardio graph, amplitudes, intervals between the peaks (a PQ interval, an RS interval, etc.), difference in amplitude between the peaks (a PQ amplitude difference, a QR amplitude difference, etc.), a period of a waveform, etc. Further, the characteristic information may be differently extracted based on the kinds of biometric signals (ECG, PCG and PPG).

The biometric signal generated in accordance with repetitive biometric motions has periodicity. In order to compress the biometric signal having periodicity, a one-period signal may be extracted, characteristic information may be generated from the extracted one-period signal, and the extracted one-period signal may be compressed. However, the extracted signal is not necessarily limited to the one-period signal. Alternatively, for example, a signal may be extracted to include at least one-period, and characteristic information may be generated from the extracted signal and compressed.

Further, the electronic apparatus 1 may include a wearable device for measuring and compressing the biometric signal and sending the compressed signal to the outside, and a display device for decompressing the compressed signal received from the wearable device and providing information to a user. For example, the wearable device such as a smart watch, etc. is worn on a body part of a user and measures a biometric signal. The display device may receive and analyze a signal from a smart phone or the like, and provides the analyzed information to a user.

FIG. 1 is a diagram illustrating an example electronic apparatus 1 which receives a measured signal from the measurer 100 via a signal line, compresses the received measured signal and generates the characteristic information.

Further, FIG. 22 is a diagram illustrating an example in which electronic apparatus 1 wirelessly receives a measured signal from the measurer 100 worn on a body part of a user. The measurer 100 may be achieved by a smart watch or the like which is worn on a wrist of a user and measures, and the electronic apparatus 1 may be achieved by a smart phone or the like which compress the measured signal received from the measurer 100, generates the characteristic information, and provide the related information to a user. Further, in this example embodiment, the measurer 100 of the electronic apparatus 1 may be achieved by at least one among a type of accessories (e.g. a ring, a bracelet, an anklet, an necklace, eye glasses, a contact lens, or a head-mounted device (HMD)), a type of textile or clothes (e.g. electronic clothes), a body attachable type (e.g. a skin pad or a tattoo), and a biometric transplant type (e.g. an implantable circuit), or the like, but is not limited thereto.

Further, FIG. 21 illustrates the electronic apparatus 1 which is worn on a body part of a user and includes the measurer 100 placed on the bottom thereof. In this example embodiment, the electronic apparatus 1 is achieved by a smart watch, which measures a biometric signal of a user through a sensor provided in the smart watch, generates the characteristic information from the measured signal, compresses and stores the measured signal, and decompresses the compressed signal in accordance with a user's selection to thereby provide related information. Alternatively, the electronic apparatus 1 may include at least one among a type of accessories (e.g. a ring, a bracelet, an anklet, an necklace, eye glasses, a contact lens, or a head-mounted device (HMD)), a type of textile or clothes (e.g. electronic clothes), a body attachable type (e.g. a skin pad or a tattoo), or a biometric transplant type (e.g. an implantable circuit), or the like, but is not limited thereto.

Figure 2:
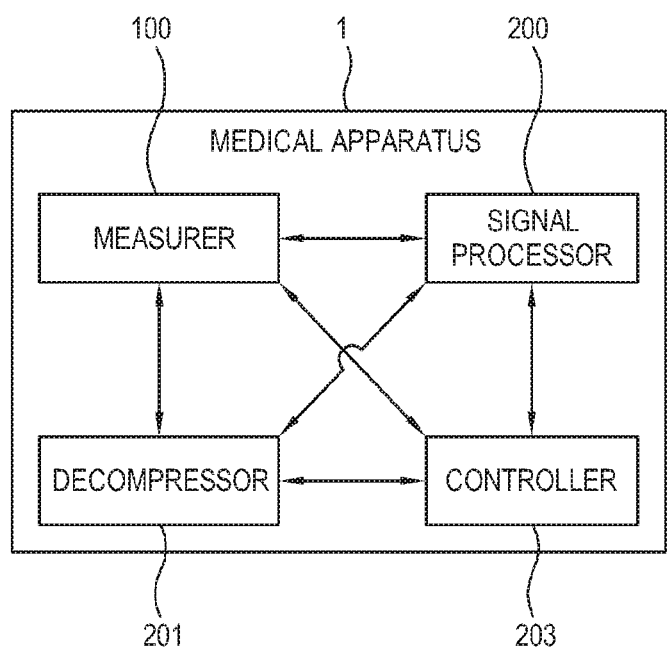
FIG. 2 is a block diagram illustrating an example electronic apparatus according to an example embodiment.

FIG. 2 is a block diagram illustrating an example electronic apparatus according to an example embodiment. As described above, the electronic apparatus 1 may be configured to measure a biometric signal of a person to be examined, generate the measured signal having a waveform corresponding to a characteristic of the biometric signal, generate at least one piece of characteristic information included in the waveform of the generated measured signal, and compress the measured signal. Further, the electronic apparatus 1 may be configured to use the characteristic information to restore a lost part of the compressed signal. To the end, the electronic apparatus 1 according to an example embodiment includes the measurer (e.g., including measuring circuitry) 100, a signal processor (e.g., including processing circuitry) 200, a decompressor (e.g., including decompressing circuitry) 201 and a controller (e.g., including processing circuitry) 203. Further, the electronic apparatus 1 may further include a power supply (or a power management integrated chip (IC), not shown) for managing power to be supplied to the electronic apparatus 1. The power supply may further include a battery (not shown). The power supply (not shown) may be charged by a wired and/or wireless method. The wireless charging method may for example include a magnetic resonance method, a magnetic induction method, a method of using electromagnetic waves, etc. For the wireless charging method, an additional circuit such as a coil loop, a resonance circuit, a rectifier, etc. may be used.

The measurer 100 may include various circuitry that measures a biometric signal of a person to be examined, and generates the measured signal having a waveform corresponding to the characteristic of the biometric signal. The measured biometric signal is transformed into a signal having an electric waveform corresponding to the characteristic of the biometric signal by various publicly known transform methods. A body part of a person to be examined, to which the measurer 100 is attached, and the kind of sensor are varied depending on the kinds of biometric signal desired to be measured. For example, the measuring circuitry of the measurer 100 for measuring the electrocardio graph may be configured to include electrodes to be attached to a chest, legs and arms of a person to be examined. Further, the measuring circuitry of the measurer 100 for measuring the phonocardio graph may be configured to include a stethoscope for sensing sound. The measuring circuitry of the measurer 100 for measuring the photoplethsymo graph may be configured to include a sensor attached to a fingertip, an ankle, etc. and sensing transparency of blood.

In this example embodiment, the measurer 100 may be placed inside the electronic apparatus 1, or may be connected to the electronic apparatus 1 by a wire such as the signal line or the like, or may wirelessly transmit the measured signal to the electronic apparatus 1. FIG. 1 illustrates the measurer 100 connected to the electronic apparatus 1 through the signal line, FIG. 22 illustrates the measurer 100 which wirelessly transmits the measured signal to the electronic apparatus 1, and FIG. 21 illustrates the measurer 100 placed in the bottom of the electronic apparatus 1.

If the measurer 100 employs the signal line to transmit a measured signal to the electronic apparatus 1 or placed in the electronic apparatus 1, there are advantages of quick transmission, little signal interference, and low power consumption. Further, if the measurer 100 wirelessly transmits a measured signal to the electronic apparatus 1 as illustrated in FIG. 22, various example embodiments are possible. For example, a measured signal generated by the measurer 100 may be transmitted to a hospital (e.g. a hospital server (not shown)) through a network, and a user's location may be tracked if it is determined that s/he has a health problem. In addition, the measured signal may be received in various devices.

The signal processor 200 is configured to process the generated measured signal. For example, the signal processor 200 may include various processing circuitry that generates at least one piece of characteristic information involved in the waveform of the measured signal, and compresses the measured signal to generate a compressed signal. For example, the characteristic information may include information related to points for medical diagnosis involved in the waveform of the measured signal, e.g., various pieces of information such as positions corresponding to peaks of the waveform of the measured signal, amplitudes of the peak, gradients of the waveform, etc. To compress the measured signal, the signal processor 200 may employ various publicly-known lossy compression methods such as, for example, and without limitation, wavelet transform, discrete sine transform, discrete cosine transform, fast Fourier transform, etc.

Further, the measured signal may refer, for example, to a signal having the characteristic of the biometric signal, which has the periodicity. To compress the measured signal, the signal processor 200 extracts a plurality of one-period signals 2000 (as illustrated, for example, in FIG. 20) from the measured waveform divided by a period, generates characteristic information from the waveform of each one-period signal 2000, and compresses each one-period signal 2000.

Further, the signal processor 200 may for example use a previously stored template to compress the plurality of one-period signals 2000. For example, the signal processor 200 may be configured to compress each one-period signal 2000 through a template of which difference from the one-period signal 2000 is lower than a threshold point.

Each compressed one-period signal 2000 may be stored in the electronic apparatus 1 or transmitted to the outside.

The present disclosure is not necessarily limited to the example of extracting the one-period signal 2000 from the measured signal. Alternatively, the electronic apparatus according to an example embodiment may generate and compress characteristic information from a signal extracted to include at least one period in accordance with settings. The decompressor 201 may include various decompression circuitry and be configured to use a decompression method corresponding to the compression method of the signal processor 200 under control of the controller 203.

For example, the decompression methods are previously stored, and the decompressor 201 selects a decompression method based on the kind of biometric signal, and uses the selected method to decompress the compressed signal.

Further, alternatively, the compressed signal transmitted from the measurer 100 may include information about the compression method for the compressed signal, and the decompressor 201 may decompress the compressed signal based on the received information about the compression method.

As described above, if the biometric signal is partially lost as the measured signal is compressed by the lossy compression, the decompressor 201 according to this example embodiment is configured to use the previously extracted characteristic information for restoring the lost part of the compressed signal. For example, the decompressor 201 decompresses the compressed signal, compares the decompressed signal with the characteristic information, determines a different part as the lost part, and restores the lost part with respect to the characteristic information, thereby decompressing the compressed signal.

For example, the measured signal may include at least one point for medical diagnosis, and the characteristic information may involve information about the at least one point for the medical diagnosis. The decompressor 201 determines whether at least one medical diagnosis point is lost in the compressed signal based on comparison with the characteristic information, and restores the lost medical diagnosis point with respect to the characteristic information, thereby decompressing the compressed signal.

If the measured signal was compressed based on the previously stored template by the signal processor 200, the decompressor 201 does not decompress the compressed signal but restores the lost characteristic information by applying the characteristic information to the previously stored template to thereby decompress the compressed signal.

Further, if the measured signal was compressed being divided into the plurality of one-period signals by the signal processor 200, the decompressor 201 decompresses the compressed signal by joining the plurality of compressed one-period signals together. Further, the characteristic information previously generated in each one-period signal may be used to restore the lost part in each one-period signal, thereby performing the decompression.

As described above, the signal processor 200 according to an example embodiment is not limited to only extraction of the one-period signal from the measured signal. Alternatively, the signal processor 200 may be configured to extract and compress a signal having at least one period in accordance with settings.

The decompressor 201 is merely provided for convenience of description, and may not have a separate physical element. For example, the decompressor 201 may be provided together with the signal processor 200 or the controller 203 to form a single chip as a system on chip (SoC), or the signal processor 200 may also serve as the decompressor 203, e.g., to decompress the compressed signal.

The electronic apparatus 1 may further include a storage that stores not only the compressed signal and the characteristic information but also health information for diagnosis. The storage may be achieved, for example, by a writable read only memory (ROM) in which data remains even though the electronic apparatus 1 is powered off, and a change is reflected. For example, the storage may be achieved by at least one of a flash memory, an erasable programmable read only memory (EPROM) or an electrically erasable programmable read only memory (EEPROM).

The controller 203 is configured to control general operations of the electronic apparatus 1. For example, the controller 203 controls the measurer 100 to measure a biometric signal of a person to be examined and generate a measured signal having a waveform corresponding to a characteristic of the biometric signal, controls the signal processor 200 to generate at least one piece of characteristic information involved in the waveform of the measured signal and compress the measured signal, and controls the decompressor 201 to decompress the compressed signal so that at least a part of the compressed signal lost by the compression can be restored based on the characteristic information. The signal processor 200 extracts the plurality of one-period signal from the measured signal having the periodicity in accordance with the characteristic of the biometric signal, generates the characteristic information from each of the plurality of extracted one-period signals, and compresses each one-period signal. As described above, the signal processor 200 may also decompress the compressed signal. Further, the controller 203 may control the operations of the signal processor 200 and the decompressor 201 based on the kind of biometric signal selected in accordance with a user's selection.

As described above, the signal processor 200 may be configured to extract a signal having at least one period from the measured signal, and generate and compress the characteristic information from the extracted signal.

Further, the controller 203 may be configured to analyze the characteristic information and the measured signal based on the health information stored in the storage, and examine health of a person to be examined (e.g. a user) to generate diagnostic information. For example, if the waveform irregularly descends or ascends between S-T peaks of the electrocardio graph, angina, myocardial infarction, etc. may be diagnosed. To this end, the electronic apparatus 1 may be configured to analyze the measured signal and provide diagnostic information that can be determined by the electronic apparatus 1.

As described above, the controller 203, the signal processor 200 and the decompressor 201 may be not provided as individual hardware components but integrated into a single chip.

In this disclosure, the example signal processor 200 may include the functions of the decompressor 201 and thus may perform all the compression of the measured signal and the generation and decompression of the characteristic information, and the controller 203 controls the operations of this signal processor 200.

The accompanying drawings and the foregoing descriptions are merely provided by way of examples, and an electronic apparatus 1 may be configured to include a first apparatus for measuring and compressing a signal, and a second apparatus for receiving and decompressing the compressed signal from the first apparatus and providing information to a user.

Figure 3:
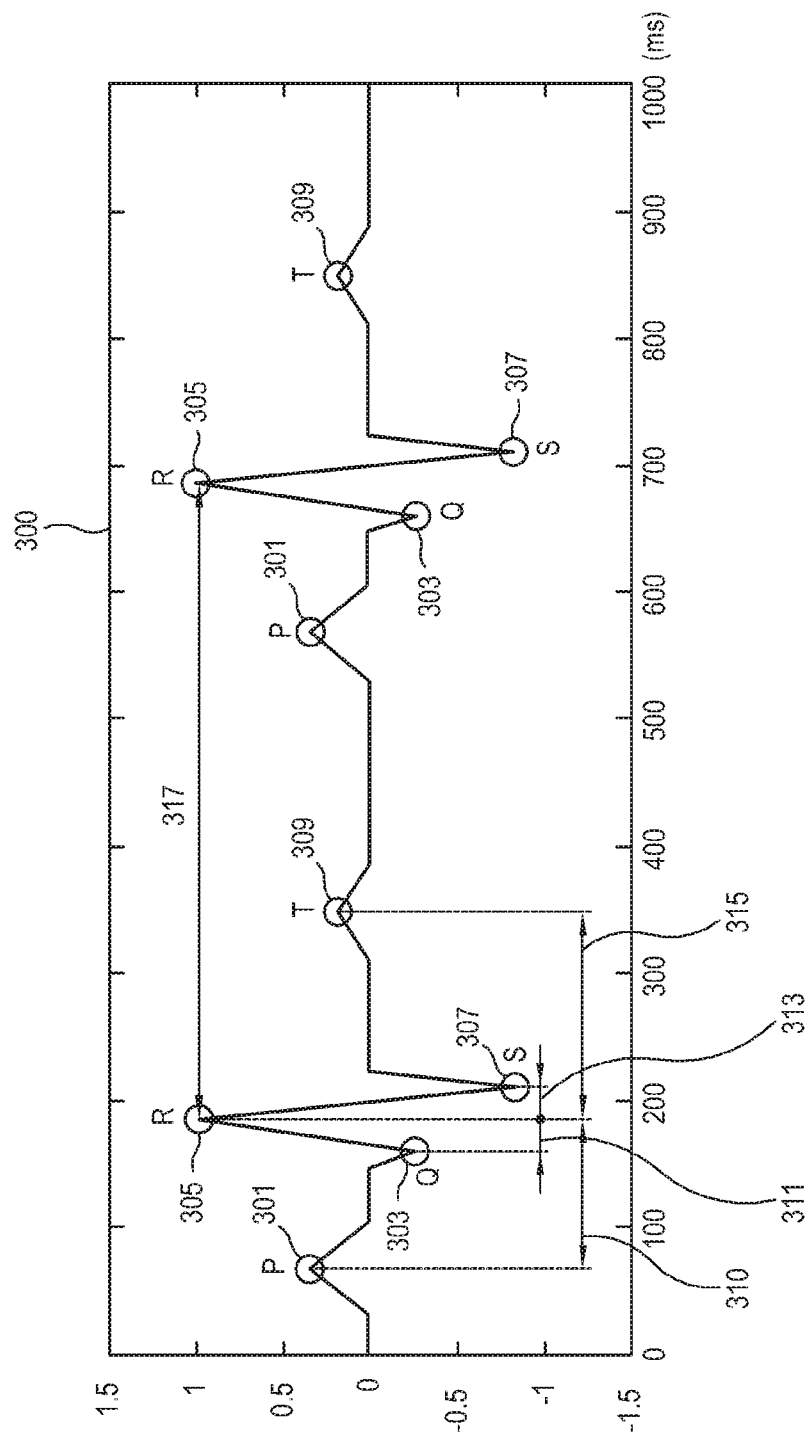
FIG. 3 is a diagram illustrating an example waveform of an electrocardio graph according to an example embodiment.
Figure 4:
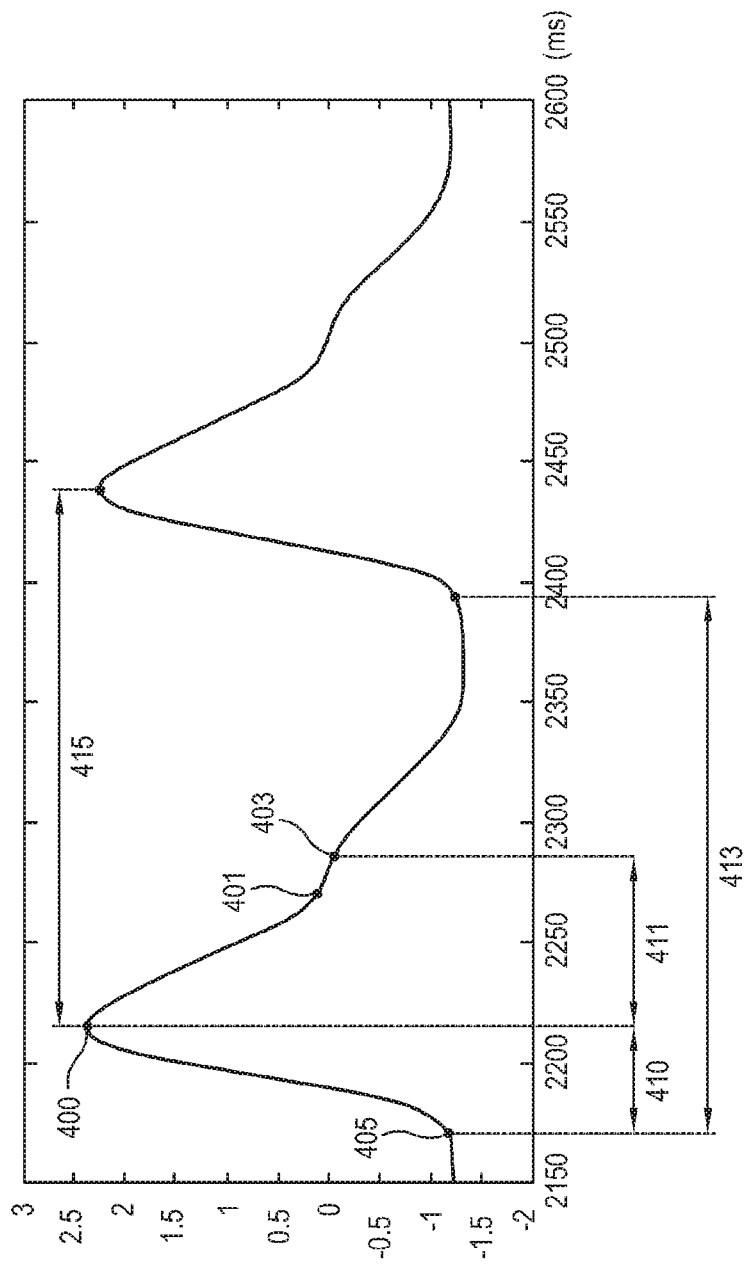
FIG. 4 is a diagram illustrating an example waveform of a photoplethsymo graph according to an example embodiment.
Figure 5:
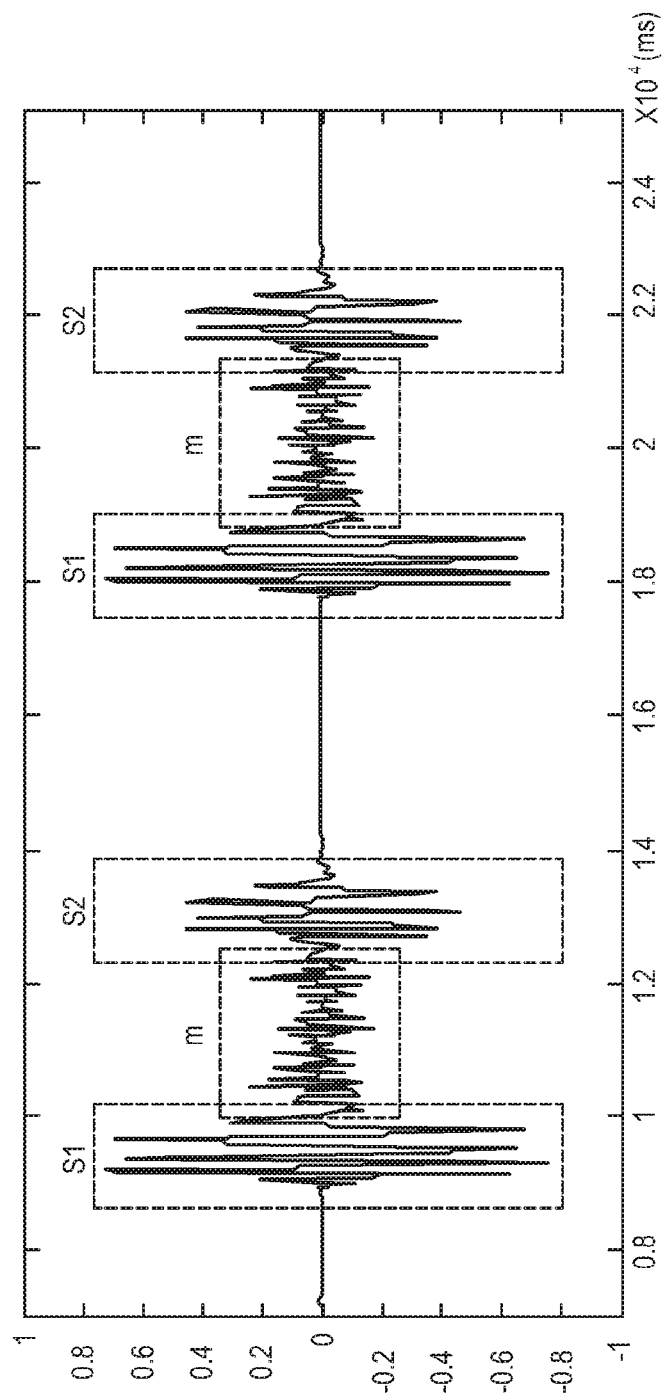
FIG. 5 is a diagram illustrating an example waveform of a phonocardio graph according to an example embodiment.
Figure 20:
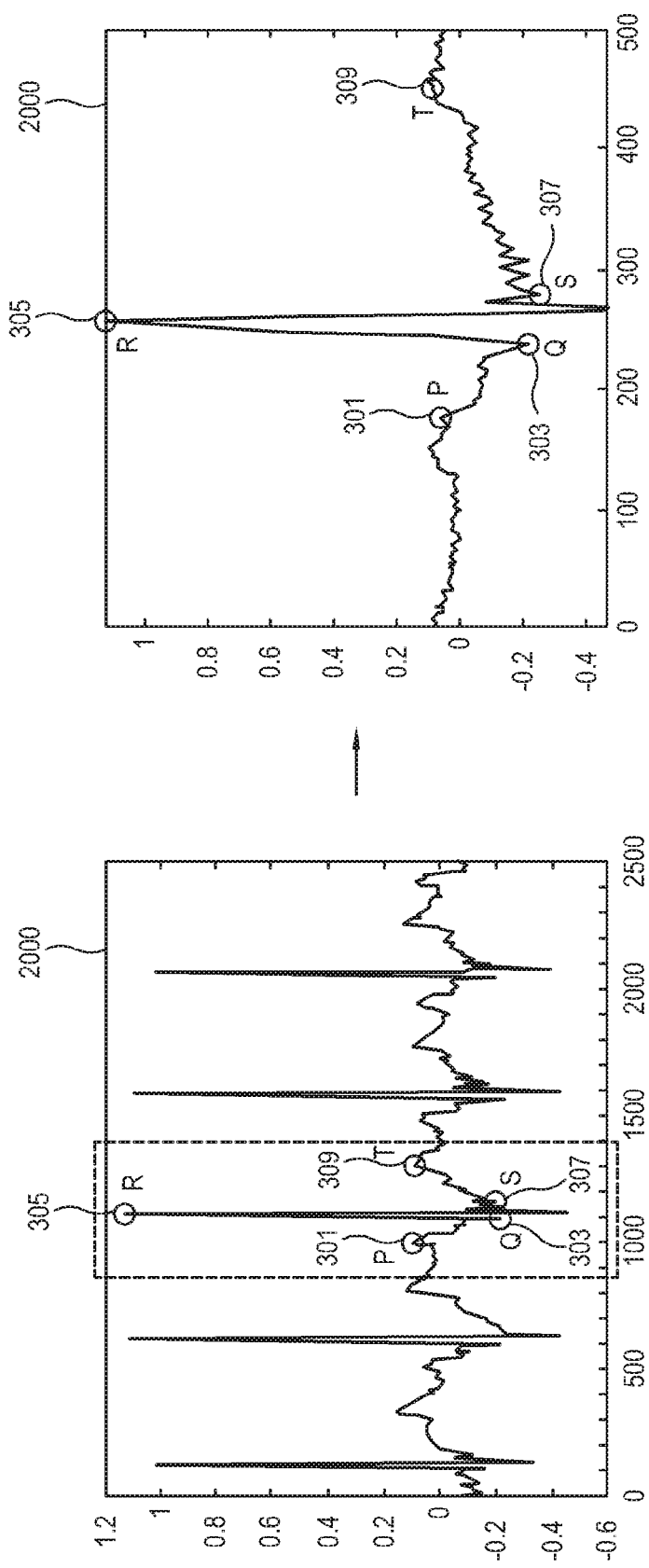
FIG. 20 is a diagram illustrating an example process of extracting a one-period signal from a measured signal having periodicity in order to compress the measured signal according to an example embodiment.

FIGS. 3, 4 and 5 illustrate example waveforms of a biometric signal, and FIG. 20 illustrates an example process of extracting a one-period signal from measured biometric signal having periodicity. FIG. 3 illustrates an example of a waveform of an electrocardio graph (ECG). The electrocardio graph is obtained by recording weak electricity, which is generated whenever a heart beats by heart pumping based on myocardial contraction, induced on a surface of a body, and includes an exercise stress electrocardio graph, an ambulatory electrocardio graph, etc. in addition to standard 12-lead electrocardio graph. The electrocardio graph test is the most used test in diagnosing circulatory diseases, and used for early diagnosis for angina, myocardial infarction or the like arrhythmia and coronary artery diseases. If the arrhythmia intermittently occurs, one-time electrocardio graph test may be insufficient to diagnose the arrhythmia, and it may be thus advantageous to obtain an electrocardio graph recorded in daily life. Therefore, the measurer 100 of the electronic apparatus 1 according to an example embodiment may be used in everyday life to compress and store the measured biometric signal, and then send the stored biometric signal to remotely consult a doctor.

A horizontal axis of the waveform indicates time, and a vertical axis indicates a voltage level due to depolarization of a heart conduction system. As a heart beats, the electrocardio graph has peaks at special points, which are called a P peak 301, a Q peak 303, an R peak 305, an S peak 307 and a T peak 309. Positions of the respective peaks 301, 303, 305, 307 and 309 on the horizontal axis, intervals 310, 311, 313, 315 and 317 between the peaks 301, 303, 305, 307 and 309, differences in amplitude between the peaks 301, 303, 305, 307 and 309, etc. are related to medical diagnosis points used in medical diagnosis. Further, the characteristic information is generated based on the medical diagnosis point.

FIG. 20 illustrates the process of extracting the one-period signal 2000 from the measured signal in order to compress the measured biometric signal having the periodicity. The electrocardio graph (ECG) is generated corresponding to heartbeats of a heart. As the heart periodically beats, the electrocardio graph (ECG) generated corresponding to the heartbeats also has the periodicity. To compress the electrocardio graph (ECG), the signal processor 200 according to an example embodiment separates a signal 2000 corresponding to one period from the measured electrocardio graph, compares the separate signal 2000 of the one period with the previously stored template, and compress a discrete wavelet transform (DWT) coefficient of a residual signal generated in accordance with comparison results. The signal processor 200 compresses not all the DWT coefficients but only some important coefficients, thereby improving compressibility.

For example, the signal processor 200 may be configured to extract the one-period signal 2000 with respect to the highest R peak among the plurality of peaks in order to cut the measured signal by the one period. The R peak 305 is the highest and acute waveform that occurs when a ventricle is depolarized. Since the signal is the electrocardio graph (ECG), the signal processor 200 detects the R peak 305. Based on the detected R peak, if a difference between the extracted one-period signal 2000 and the template is higher than the threshold point, the signal processor 200 stores the one-period signal 2000 as a new template. On the other hand, if the difference is not higher than the threshold point, the selected template is used in the compression. As described above, the signal processor 200 obtains difference between the selected template and the one-period signal 2000, and compresses the DWT coefficient of the residual signal generated due to the difference, thereby finishing the compression of the electrocardio graph (ECG).

Figure 8:
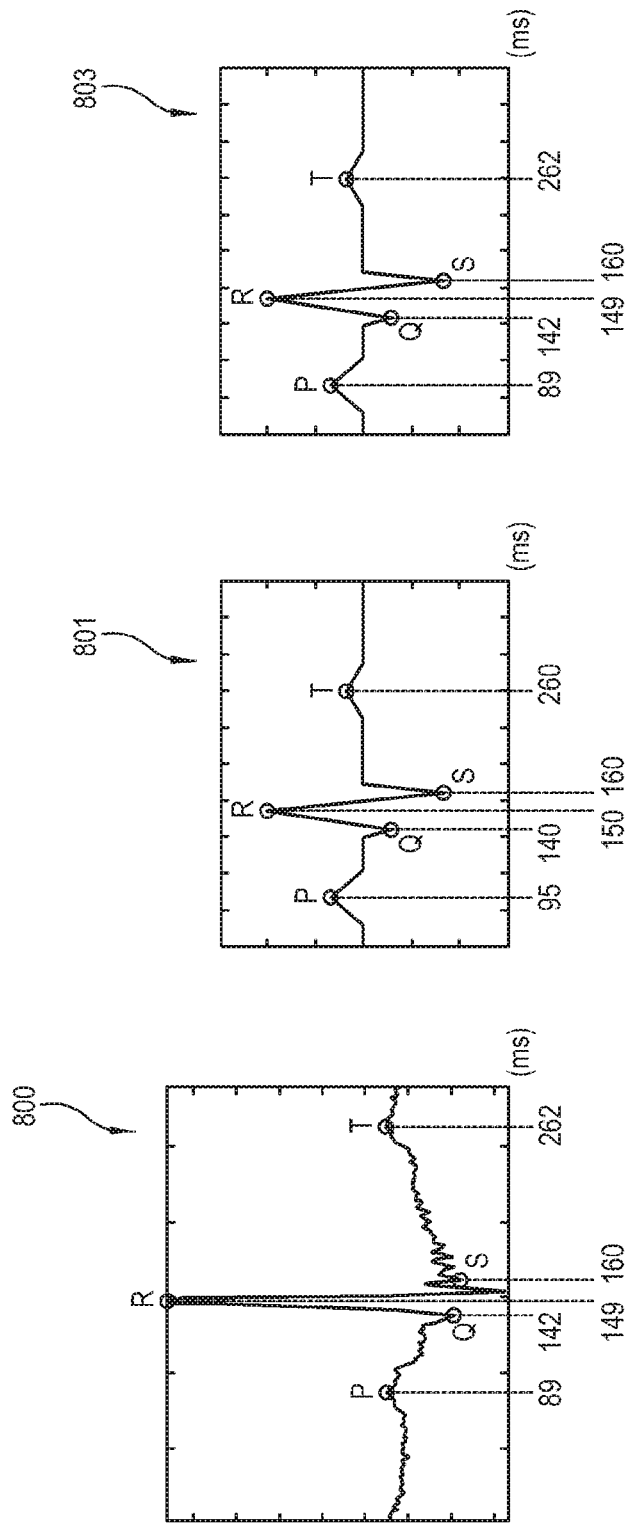
FIG. 8 is a diagram illustrating example compression and decompression of an electrocardio graph according to an example embodiment.

FIG. 8 illustrates a measured signal 800 extracted corresponding to one period and a selected template 801. Although the difference between the measured signal 800 extracted corresponding to one period A and the selected template 801 is not higher than the threshold point, there is a little difference in light of a peak time, etc. and this causes a loss of the characteristic information, which will be described later.

This example embodiment illustrates an example where the signal processor 200 extracts the plurality of one-period signals from the measured signal, but the scope of the present disclosure is not limited to the foregoing example embodiment and drawings. As described above, the signal processor 200 according to an example embodiment may be configured to extract a plurality of signals having a plurality of periods less than the measured signal or at least one period from the periodic measured signal having the characteristic of the biometric signal having a plurality of periods, generate the characteristic information from the extracted signal having the plurality of periods, and compress the signal having the plurality of periods.

FIG. 4 illustrates the waveform of the photoplethysymo graph (PPG). Pressure generated by heartbeats causes blood to flow in a blood vessel. Whenever a heart beats, the pressure works up to a distal capillary vessel of a body, e.g., up to a blood vessel of a fingertip. Arterial blood in the capillary vessel at the fingertip is supplied to a cellular tissue, enters a vein and returns to the heart. An arterial blood volume in the blood vessel at the fingertip repetitively increases and decreases in sync with the heartbeats. When a light source emits light to the finger, a partial amount of light is absorbed in blood, bones and tissues, and the other amount of light passes through them and reaches a light receiver. The amount of absorbed light is proportional to the amount of skin, tissues and blood in the path of the light. However, there are no changes in the amount of skin and tissues except change in a stream of blood due to the heartbeats. Therefore, the amount of absorbed light is varied depending on the blood steam. Since the amount of passed light detected in the light receiver comes from excluding the amount of light absorbed in the finger from the light emitted from the light source, variation in the amount of passed light reflects change in the blood stream. Thus, it is possible to detect variation in the blood volume synchronizing with the heartbeats by measuring the amount of light received in the light receiver, and a waveform corresponding to the change in the blood volume detected by measuring the amount of light will be called the photoplethsymo graph.

Like the electrocardio graph, a horizontal axis indicates time, and a vertical axis indicates the amount of detected light. As a heart beats, the photoplethsymo graph (PPG) have peaks at specific points, which are respectively called a systole peak 400, a diastolic peak 403, an imposed notch 401 and a hall 405. Positions of the peaks 400, 401 and 403 and intervals 410, 411, 413 and 415 between the peaks 400, 401 and 403 are related to medical diagnosis points for medical diagnosis, and thus have to be retained as the characteristic information not to be lost in the compression.

The photoplethsymo graph (PPG) also has periodicity. In order to compress the photoplethsymo graph (PPG), like the compression of the electrocardio graph (ECG), the signal processor 200 according to an example embodiment may be configured to extract a signal having one period, compares the extracted one-period signal and the previously stored template, and compresses the DWT coefficient of the residual signal.

FIG. 5 illustrates the waveform of the phonocardio graph (PCG). The phonocardio graph is obtained by recording a heart sound and a heart murmur, which is recorded simultaneously with the electrocardio graph and visualizes auscultation to diagnose various heart diseases. The phonocardio graph is useful in a heart valve disease, an inherent heart disease, etc., and thus has to be retained not to be lost.

The heart sound is classified into a first heart sound S1 made during a ventricle contraction period, a second heart sound S2 made during a ventricle diastolic period, a heart murmur made between the first heart sound and the second heart sound when a blood stream passes through heart valves or blood vessels. The heart murmur is also classified into innocent and functional heart murmurs and a diseased heart murmur due to a symptom of illness. The diseased heart murmur may be caused when a heart structure has a hole, when valves are loose to thereby cause regurgitation, when valves are too narrow, or by a structural problem in the heart valves or the heart.

The heart murmur is feebler than the heart sound, and is therefore likely to be lost as it is treated as general noise when the phonocardio graph is compressed. Thus, the heart murmur has to be retained not to be lost during the compression. In the phonocardio graph, positions and levels of such a heart murmur are regarded as the characteristic information.

For example, the phonocardio graph (PCG) is also generated as a heart beats, and thus has periodicity. To compress the phonocardio graph (PCG), the signal processor 200 extracts the one-period signal from the measured phonocardio graph (PCG), transforms the extracted one-period signal into a signal of a frequency domain through the wavelet transform or the like, and generates a signal transformed by combination of the coefficient and the generating function. Then, the signal processor 200 performs thresholding for removing all the signals of which coefficient is not higher than a threshold value, thereby compressing the phonocardio graph (PCG). While thresholding the transformed signal, if a level of a heart murmur is not higher than the threshold value, it is regarded as general added noise and thus removed. Therefore, the positions, the levels, etc. of the heart murmur and the like characteristic information for the medical diagnosis have to be retained.

Figure 6:
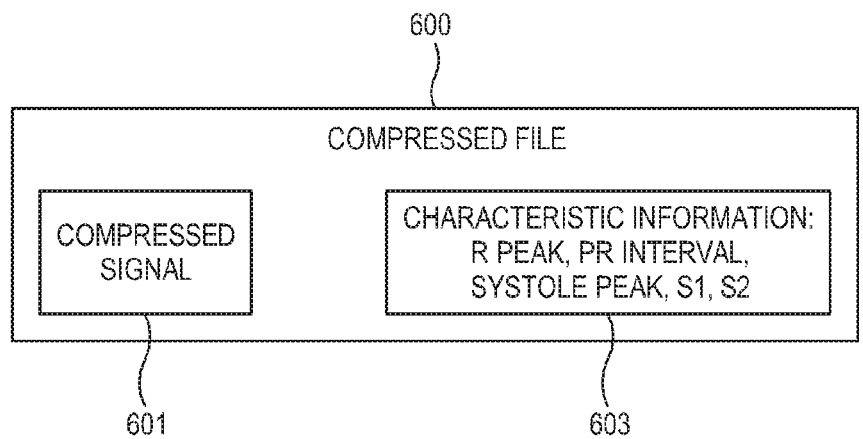
FIG. 6 is a diagram illustrating an example compressed file according to an example embodiment.

FIG. 6 illustrates an example of a compressed file according to an example embodiment. The compressed file 600 generated by processing the measured signal in the signal processor 200 includes a compressed signal 601 and at least one piece of characteristic information 603 involved in the waveform of the measured signal.

The compressed signal 601 is generated by compressing the measured signal, and the characteristic information 603 is extracted from the measured signal. The compressed signal 601 and the characteristic information 603 may be stored as a file 600 and transmitted.

As illustrated in FIG. 6, the characteristic information 603 may refer, for example, to information involved in the waveform of the measured signal, and includes information related to points to be medically diagnosed in the measured signal. The characteristic information 603 may be differently applied in accordance with the measured biometric signals. For example, in case of the electrocardio graph (ECG), the points of the waveform for the medical diagnosis includes time of when peaks occurs, an interval between the peaks, difference in amplitude between the peaks, etc. In case of the phonocardio graph (PCG), the points of the waveform for the medical diagnosis includes positions of the first heart sound and the second heart sound, an interval between the heart sounds, a position of a heart murmur, a level of a heart murmur, etc. Thus, the characteristic information 603 to be stored is varied depending on the biometric signal.

Figure 7:
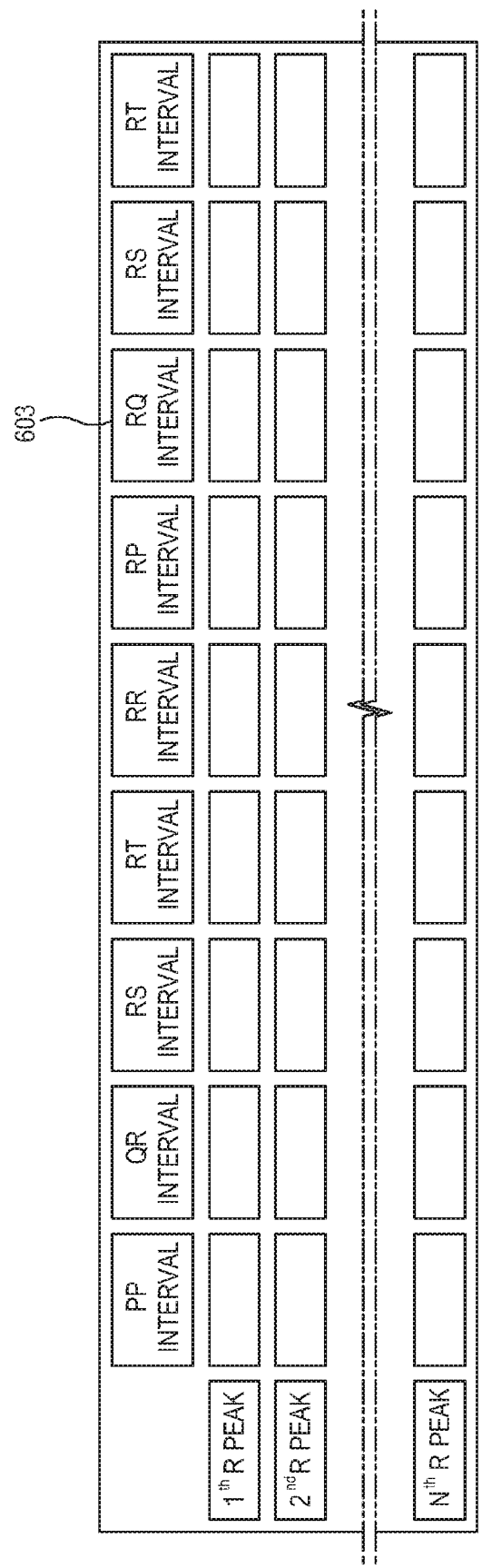
FIG. 7 is a diagram illustrating example characteristic information according to an example embodiment.

This example embodiment illustrates the characteristic information 603 in the case of the electrocardio graph (ECG). The electrocardio graph (ECG) has the periodicity. In the electrocardio graph (ECG), the vertical axis indicates the nth period, i.e. the nth R peak since the period is measured with respect to the R peak, and the horizontal axis indicates the points for the medical diagnosis. For example, the 1st R peak refers to the first period in the measured electrocardio graph (ECG), the PP interval refers to the interval between the P peaks, and the QR interval refers to the interval between the Q peak and the R peak. FIG. 7 illustrates only the characteristic information 603 of the electrocardio graph (ECG), but the kind of biometric signal for generating the characteristic information 603 is not limited to the electrocardio graph (ECG). Alternatively, the characteristic information 603 may be generated based on various biometric signals. Further, the characteristic information 603 may be generated based on various medical diagnosis points in accordance with the kinds of measured biometric signal. Further, the medical diagnosis point is not limited to only the interval between the peaks as shown in FIG. 7. As mentioned above, the medical diagnosis point may include the time of when the peaks occur, the amplitude of the peak, and the like information.

Accordingly, the present disclosure is not limited to FIG. 7, and various pieces of characteristic information may be extracted and stored from various kinds of biometric signals.

FIG. 8 illustrates the process of compressing and decompressing the electrocardio graph according to an example embodiment. The measured electrocardio graph (ECG) signal 800 refers to a biometric signal measured by the measurer 100. As described above, the electrocardio graph (ECG) signal has the periodicity. The signal 800 measured by the measurer 100 includes noise and is thus difficult to be used in the medical diagnosis. Therefore, the signal processor 200 according to an example embodiment may be configured to use a previously stored template and selects a template the most similar to the measured signal 800 as a corresponding waveform in order to compress the measured electrocardio graph. To this end, the signal processor 200 may be configured to extract a one-period signal from the measured electrocardio graph (ECG). FIG. 20 illustrates a process of extracting the one-period signal 2000 from the measured electrocardio graph (ECG). The signal processor 200 extracts the one-period signal 2000, applies a template, of which difference from the extracted one-period signal 2000 is not higher than the threshold point, to the extracted one-period signal 2000, and compresses the electrocardio graph (ECG) based on the DWT coefficient of the residual signal, e.g., the difference between the one-period signal 2000 and the template. The compressed signal 801 generated through this process is similar to the measured signal 800. However, a loss in the compression may cause a little difference between the compressed signal 801 and the measured signal 800 with respect to at least one specific point for the medical diagnosis in the waveform. Since the biometric signal has the periodicity, the compression may be performed by respectively applying the templates, of which differences from the plurality of extracted one-period signals 2000 are not higher than the threshold point, to the plurality of extracted one-period signals 2000. The compressed signals obtained by respectively applying the templates to the plurality of extracted one-period signals 2000 may be combined into a single signal or may be individually stored. Then, the decompressor 201 applies the extracted characteristic information to the compressed signal 801, and restores a lost part so that the measured signal 800 and the decompressed signal 803 cannot be different in the medical diagnosis point of the waveform, thereby performing the decompression. During the decompression, the decompressor 201 decompresses the separated compressed signals 801 respectively stored as the one-period signals 2000 into a single waveform. According to another example embodiment, the decompressed signal may be given as information or the like to a user.

Referring to FIG. 8, the measured signal 800 has the medical diagnosis points, e.g., the P peak at 89 ms, the Q peak at 142 ms, the R peak at 149 ms, the S peak at 160 ms and the T peak at 262 ms, but the compressed signal 801 has the P peak at 95 ms and the R peak at 150 ms. In addition, other peaks of the compressed signal 801 are also different in time from those of the measured signal 800 (e.g., Q peak at 140 ms, S peak at 160 ms and T peak at 260 ms). If the compressed signal 801 is decompressed using the characteristic information, the decompressed signal 803 includes the P peak at 89 ms and the R peak at 149 ms like those of the measured signal 800. Likewise, other peaks of the decompressed signal 803 occur at the same time as those of the measured signal 800.

The foregoing description and drawings are just given by way of example. According to another example embodiment, in consideration of an information loss, the signal processor 200 may be configured to extract the characteristic information about the amplitude or the like of each peak or extract the information about the gradient or the like of the waveform, and the decompressor 201 may be configured to decompress a signal based on the extracted information.

Like the electrocardio graph (ECG), the photoplethsymo graph (PPG) has periodicity, uses a peak value, an interval between peaks, etc. as the characteristic information, and undergoes the compression process similar to that for the electrocardio graph (ECG). Therefore, detailed descriptions about this will be omitted.

FIG. 9 illustrates an example processes of compressing and decompressing the phonocardio graph according to an example embodiment. Since a heart murmur also has periodicity, the one-period signals are extracted, and then the wavelet transform using the coefficient and the base function is applied to the extracted one-period signals according to frequency bands, thereby compressing the phonocardio graph. Although the measured signal 900 includes a heart murmur 910, if the signal processor 200 applies the lossy compression to the measured signal 900, the measured signal 900 is compressed into a signal 901, from which a heart murmur 910 is removed 911 by regarding the heart murmur 910 not higher than a threshold level as noise. Therefore, the decompressor 201 according to an example embodiment extracts the position and level of the heart murmur 910 into the characteristic information, and restores the removed heart murmur 910 in the waveform during the decompression for the medical diagnosis, thereby generating a decompressed signal 903.

In FIG. 9, the measured signal 900 includes the heart murmur 910, but the compressed signal 901 includes no heart murmur since the heart murmur is regarded as noise and removed 911. However, the decompressed signal 903 is restored using the position and level of the heart murmur 910 as the characteristic information about the medical diagnosis points of the measured signal 900, and thus includes the heart murmur 913 like the measured signal 900.

According to another example embodiment, the controller 200 may be configured to control the position or level of the heart murmur 913 in accordance with a user's selection during the decompression to include the heart murmur 913.

Figure 10:
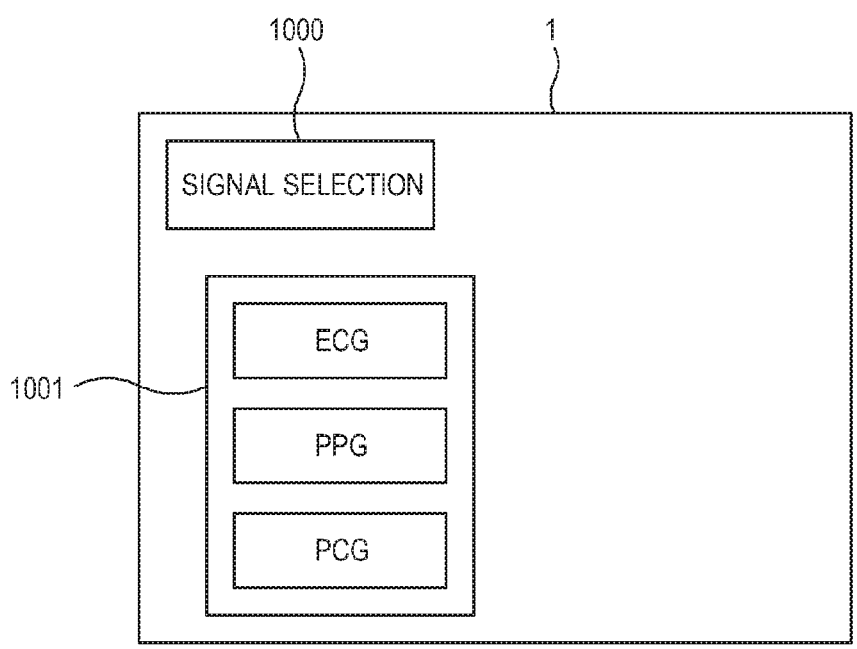
FIG. 10 is a diagram illustrating an example of a user interface provided to a user according to an example embodiment.

FIG. 10 illustrates an example user interface through which a user can select the kind of biometric signal measured according to an example embodiment. In this example embodiment, the kind of biometric signal includes an electrocardio graph, a photoplethsymo graph, a phonocardio graph, an electroencephalogram, blood pressure, a bloodstream, blood sugar, a body temperature, oxygen saturation, skin resistance, an electromyogram (EMG), or a pupillary motion. Theses biometric signals are just given by way of example, and there are no limits to the biometric signals.

As described above, the electronic apparatus 1 according to an example embodiment may be configured to measure and process various kinds of biometric signal. Further, the electronic apparatus 1 may provide the user interface including a guide 1000 and a menu item 1001 for allowing a user to previously select what signal to be measured, and a user selects the menu item 1001 corresponding to the kind of the biometric signal to be measured, thereby sending a control command to the electronic apparatus 1.

The electronic apparatus 1 is configured to compress and decompress a measured signal in accordance with a user's selection. For example, if a biometric signal to be measured is the electrocardio graph (ECG), the controller 203 of the electronic apparatus 1 controls the signal processor 200 to detect an R peak from the measured signal, extract a one-period signal ('2000' in FIG. 20) based on the detected R peak, generate the characteristic information from the extracted one-period signal 2000, and apply the lossy compression to the one-period signal 2000. If a biometric signal to be measured is the photoplethsymo graph (PPG), the controller 203 may control the signal processor 200 to generate a one-period signal based on another reference or use another transform or compression method as necessary. According to this example embodiment, the biometric signal to be measured may be determined based on a user's input, or the controller 203 may determine the kind of biometric signal to be measured based on the measured signal received from the measurer 100. In addition, the controller 203 may previously determine the kind of biometric signal to be measured in accordance with a sensor or the like provided in the measurer 100.

Figure 11:
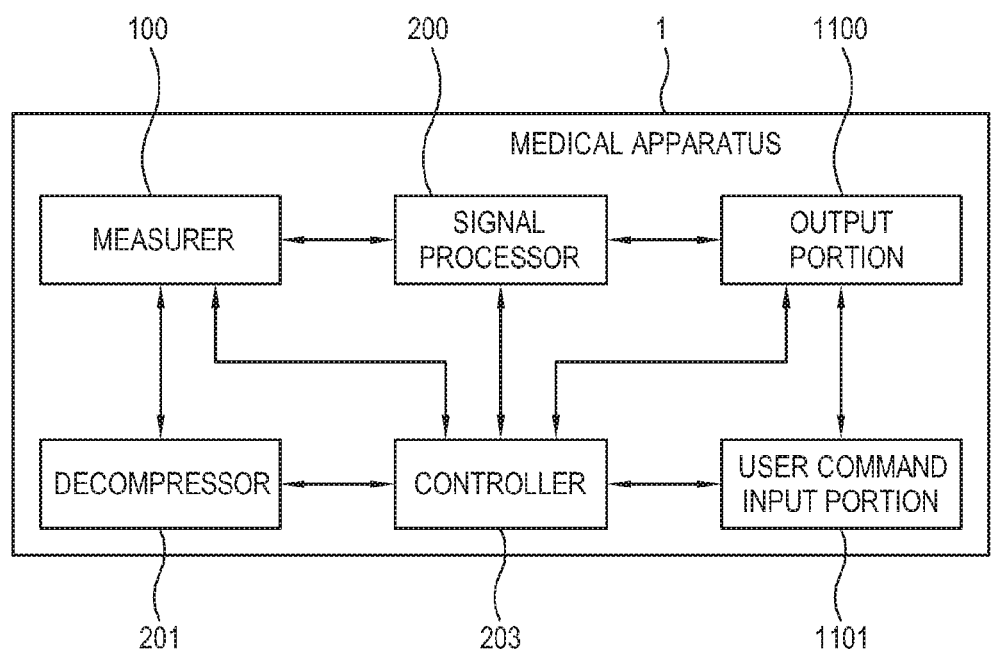
FIG. 11 is a block diagram illustrating an example electronic apparatus with an output portion according to an example embodiment.

FIG. 11 is a block diagram illustrating an example medical apparatus according to an example embodiment. The electronic apparatus 1 measures a biometric signal selected based on a user's control command, compresses the measured signal while generating the characteristic information corresponding to medical diagnosis points in the measured signal based on the selected biometric signal, decompresses the compressed signal in accordance with the characteristic information, and outputs and provides at least one among the characteristic information, the diagnostic information and the decompressed signal to a user. The electronic apparatus 1 may be achieved by various smart devices for offering health care service, such as a smart phone, a wearable device, a health patch attached to a body and measuring a heartbeat, breathing and movement; and a computed tomography (CT) device, a magnetic resonance imaging (MRI) device, or the like precisely manufactured to be used in a hospital, etc. If the electronic apparatus 1 is achieved by a smart device, a user may always wear the electronic apparatus 1 and thus a biometric signal of a user is collected for a long time. For example, information related to the collected biometric signal may help diagnosis. For example, angina, myocardial infarction or the like specific heart disease is likely to be overlooked in a hospital since it has little symptoms in a daily life, but may be discovered by a specific waveform in the electrocardio graph in everyday life. Thus, such a smart device is useful in case of a patient suspected of heart diseases.

The electronic apparatus 1 not only measures and compresses a biometric signal, but also decompresses the compressed signal and analyzes the decompressed signal, thereby providing analysis results to a user. To this end, the electronic apparatus 1 according to an example embodiment may further include an output portion 1100 including various output circuitry and a user command input portion 1101 including various input circuitry.

The output portion 1100 is configured to provide various pieces of information such as the characteristic information, the diagnostic information and the decompressed signal to a user. The output portion 1100 may include various output circuitry, such as, for example, and without limitation, at least one of a display for displaying an image, and a loudspeaker for outputting a sound. The display is configured to display a waveform of the decompressed signal restored from the compressed signal, expresses the characteristic information in numerals, and display diagnostic information analyzed based on the characteristic information and the measured signal. To this end, the display may include a panel, a driving circuit, etc. The loudspeaker is configured to make a sound based on the diagnostic information related to the decompressed signal and a sound based on the decompressed signal. The loudspeaker may be placed inside the electronic apparatus 1, or may be provided as a separate device connected to the electronic apparatus 1 through a signal line or the like.

The user command input portion 1101 may include various input circuitry and be configured to directly receive a control command through a control panel or remotely receive a remote control signal including a user's control command from a remote controller. The user command input portion 1101 may include various other input circuitry, such as, for example, and without limitation, a touch pad, or a touch screen for sensing a user's touch on the display. The user command input portion 1101 may further include a microphone or the like for recognizing a user's voice command. A user may use the user command input portion 1101 to select the kind of biometric signal to be measured, control the electronic apparatus 1 to compress or decompress the measured signal, or issue a command to output desired information through the output portion 1100. Further, a user may use the user command input portion 1101 to change the characteristic information, and control the electronic apparatus 1 to restore the compressed signal based on the changed characteristic information.

The controller 203 controls the signal processor 200 to change the characteristic information based on a user's command received through the user command input portion 1101, and controls the decompressor 201 to decompress the compressed signal by restoring the medical diagnosis point lost in the compression based on the changed characteristic information. For example, the change in the characteristic information refers to position adjustment of the peak in the electrocardio graph (ECG), amplification or removal of the heart murmur in the phonocardio graph (PCG), or the like adjustment in the extracted characteristic information. As necessary, a user may input a control command through the user command input portion 1101, thereby controlling the electronic apparatus 1 to change the characteristic information, decompress the compressed signal to include the changed characteristic information, and output the decompressed signal including the changed characteristic information.

According to another example embodiment, the electronic apparatus 1 may be configured to decompress a signal, of which at least one medical diagnosis point is lost, without using the generated characteristic information 603 (referring to FIG. 6), and output the decompressed signal and the characteristic information. For example, the decompressor 201 in this example embodiment decompresses the compressed signal without using the characteristic information in the state that the medical diagnosis point is lost, and the output portion 1100 outputs the signal, of which the medical diagnosis point is lost, and the characteristic information. Although the medical diagnosis point is a little lost, a user can get important information from the characteristic information output while referring to only the shape of the waveform of the measured signal.

Figure 12:
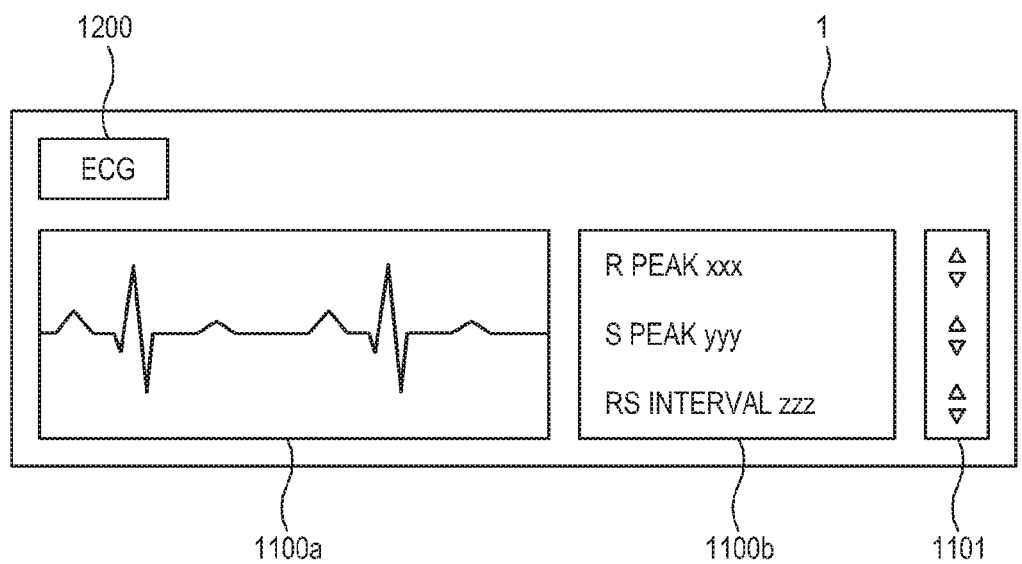
FIG. 12 is a diagram illustrating an example of an electronic apparatus according to an example embodiment, in which a decompressed signal and characteristic information are provided to a user, and the characteristic information is adjustable.
Figure 13:
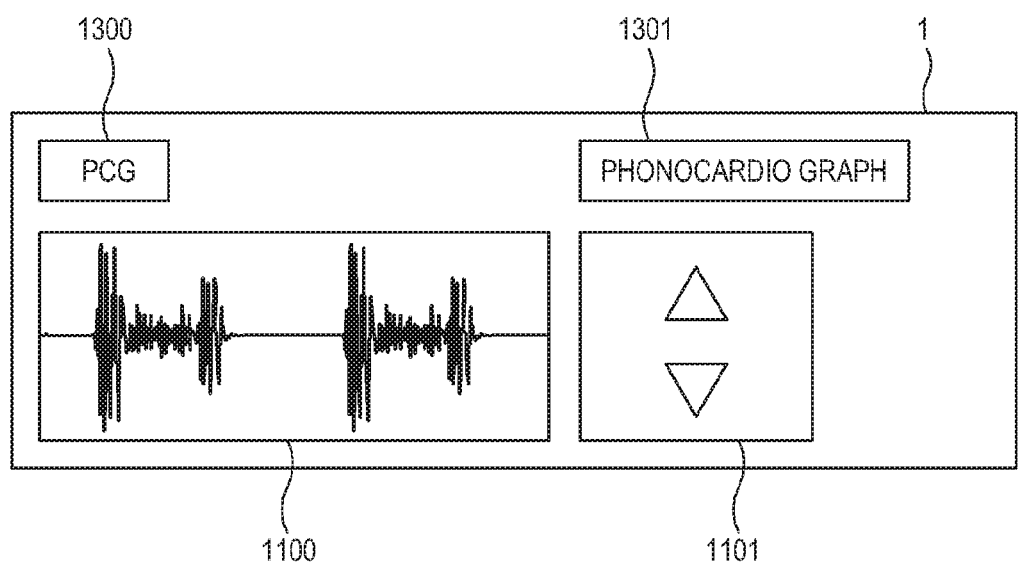
FIG. 13 is a diagram illustrating an example of an electronic apparatus according to an example embodiment, in which a decompressed signal and characteristic information are provided to a user, and the characteristic information is adjustable.

FIGS. 12 and 13 are diagrams illustrating an example medical apparatus according to an example embodiment. The electronic apparatus 1 may provide information about the diagnostic information, the decompressed signal or the characteristic information through the output portion 1100.

FIG. 12 is a diagram illustrating an example where a selected biometric signal is the electrocardio graph (ECG). As described above, the electronic apparatus 1 may include output portions 1100*a* and 1100*b* and the user command input portion 1101. The output portions 1100*a* and 1100*b* may be configured to provide a user interface including a guide 1200 showing the kind of biometric signal, a waveform 1100*a* of a decompressed signal, and characteristic information 1100*b* of the biometric signal. The electronic apparatus 1 may be configured to decompress the measured signal using the characteristic information changed in accordance with a user's selection and output it to the output portion 1100*a* and 1100*b*. Further, the user command input portion 1101 may be configured to adjust and change the characteristic information 1100*b* in response to a user's command. In this example embodiment, the characteristic information, i.e. the position of the R peak on the time axis may be adjusted or the RS interval may become narrower or wider in response to a user's command.

FIG. 13 illustrates an example where a selected biometric signal is the phonocardio graph (PCG). The electronic apparatus 1 may include an output portion 1100 and a user command input portion 1101. The output portion 1100 may be configured to output a user interface including a guide 1300 for showing the kind of biometric signal and a guide 1301 for informing that the characteristic information 603 is adjustable, and a waveform 1100 of a decompressed signal to a user. The user command input portion 1101 is configured to adjust and change the level or position of the heart murmur in response to a user's command. In this example embodiment, the characteristic information, i.e., the position of the heart murmur on the frequency domain may be adjusted or the level of the heart murmur may be changed in response to a user's command.

In this example embodiment, the output portion 1100 and the user command input portion 1101 are just given by way of example. Alternatively, the output portion 1100 of providing information to a user and the user command input portion 1101 of receiving a control command from a user may be achieved in various forms.

According to another example embodiment, the controller 203 analyzes a user's health based on the characteristic information 603 and the stored health information, and controls the output portion 1100 to generate and output the diagnostic information. The diagnostic information may for example inform a user that s/he is suspected of angina or other heart diseases and advise him/her to see a doctor.

Figure 14:
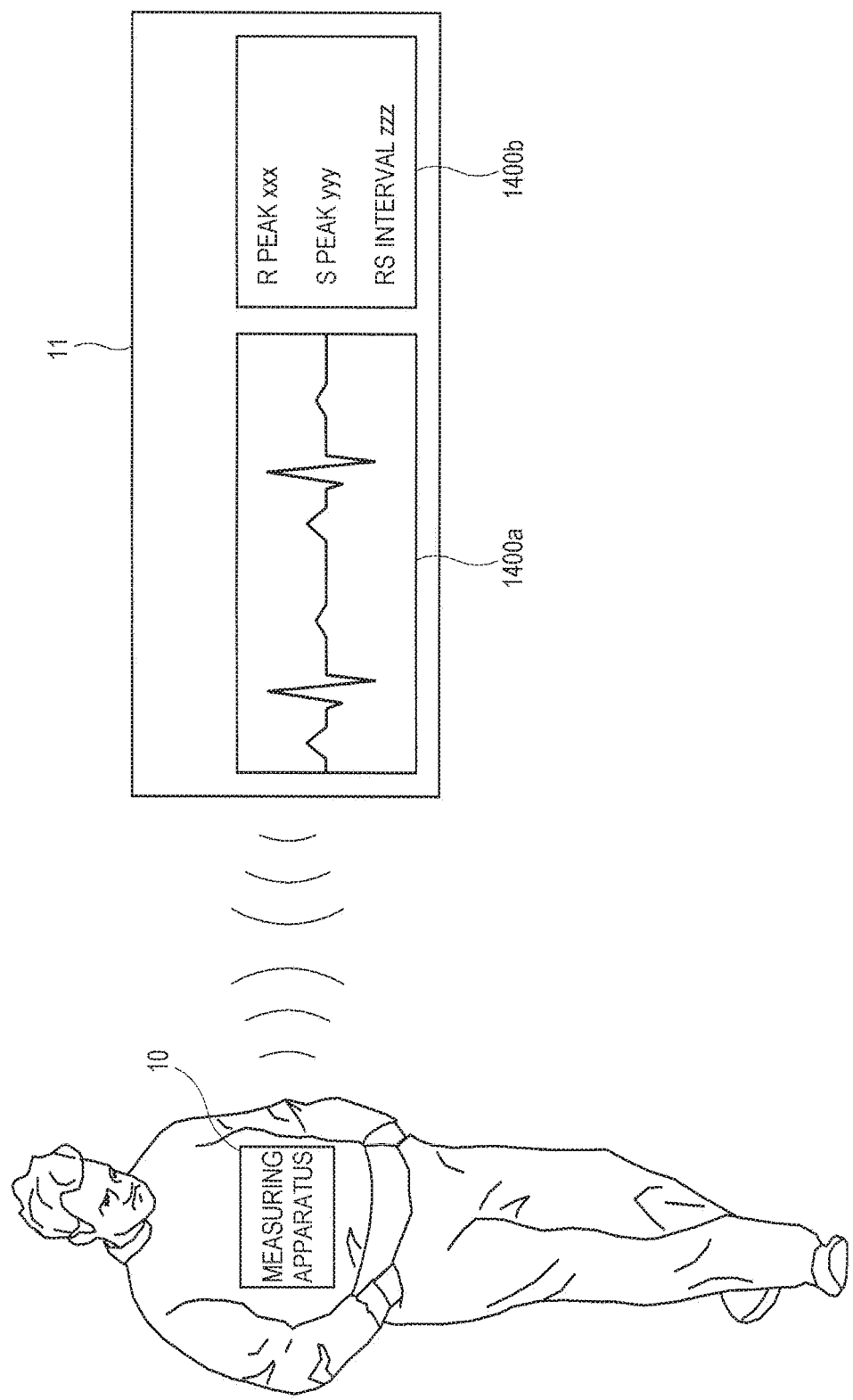
FIG. 14 is a diagram illustrating an example of an apparatus for measuring a biometric signal and an apparatus for decompressing the biometric signal according to an example embodiment.

FIG. 14 is a diagram illustrating an example apparatus for measuring a biometric signal and an apparatus for decompressing the biometric signal according to another example embodiment. A medical diagnosis system for diagnosing a user's health may include a biometric signal measuring apparatus 10 and a biometric signal decompressing apparatus 11. The biometric signal measuring apparatus 10 measures a biometric signal of a person to be examined, generates the measured signal having the waveform corresponding to the characteristic of the biometric signal, extracts the characteristic information related to the medical diagnosis points included in the waveform of the measured signal, compresses the measured signal, and transmits the compressed signal and the characteristic information to the biometric signal decompressing apparatus 11. The biometric signal decompressing apparatus 11 receives the characteristic information and the compressed signal from the biometric signal measuring apparatus 10, decompresses the compressed signal based on the characteristic information, and provides the decompressed signal and the characteristic information to a user through an output portion 1400. The output portion 1400 may include output portions 1400*a* and 1400*b*. 1400*a* may display a signal and 1400*b* may include the characteristic information.

The biometric signal measuring apparatus 10 may include a wearable device such as a band to be worn on a body part of a user, a smart watch, etc. Further, in this example embodiment, the biometric signal measuring apparatus 10 may be achieved by at least one among a type of accessories (e.g. a ring, a bracelet, an anklet, an necklace, eye glasses, a contact lens, or a head-mounted device (HMD)), a type of textile or clothes (e.g. electronic clothes), a body attachable type (e.g. a skin pad or a tattoo), and a biometric transplant type (e.g. an implantable circuit), or the like, but is not limited thereto.

The biometric signal decompressing apparatus 11 may include a computer, a smart phone, or the like which decompresses the measured signal and provides the diagnostic information to a user based on the decompressed signal. In this example embodiment, the biometric signal decompressing apparatus 100, which decompresses the measured signal and provides the diagnostic information to a user based on the decompressed signal, may include a tablet personal computer (PC), a mobile phone, a video phone, an E-book reader, a desktop computer, a laptop computer, a netbook computer, a workstation, a server, a personal digital assistant (PDA), a portable multimedia player (PMP), an MP3 player, a mobile medical apparatus, or a camera, or the like, but is not limited thereto. Further, the biometric signal decompressing apparatus 100 in this example embodiment may include home appliances. For example, the home appliances may include a television, a digital versatile disc (DVD) player, an audio system, a refrigerator, an air conditioner, a cleaner, an oven, a microwave oven, a washing machine, an air cleaner, a set-top box, a home automation control panel, a security control panel, or an electronic frame, or the like, but is not limited thereto.

Such a system including the biometric signal measuring apparatus and the biometric signal decompressing apparatus is useful in diagnosing a disease without going to a hospital when a person to be examined and a doctor are far away from each other. For example, a user always wears the biometric signal measuring apparatus 10 in daily life, and the measured signal is periodically sent to the biometric signal decompressing apparatus 11 of the hospital.

Figure 15:
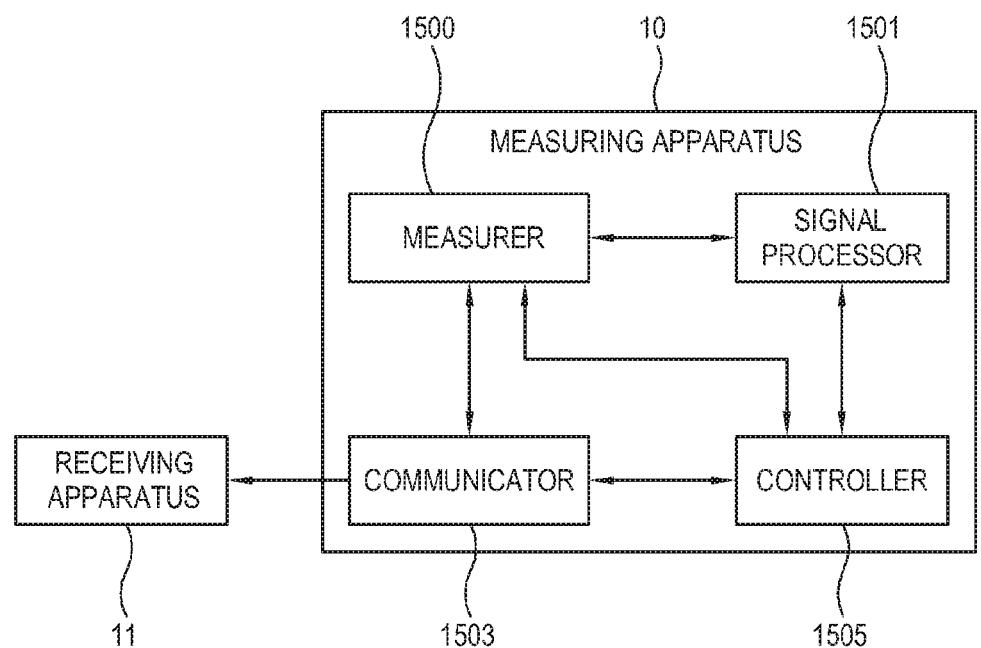
FIG. 15 is a block diagram illustrating an example apparatus for measuring a biometric signal according to an example embodiment.

FIG. 15 is a block diagram illustrating an example biometric signal measuring apparatus according to another example embodiment. The biometric signal measuring apparatus is configured using some elements of the foregoing electronic apparatus 1. For example, the biometric signal measuring apparatus 10 includes a measurer (e.g., including measuring circuitry) 1500, a signal processor (e.g., including processing circuitry) 1501 and a controller (e.g., including processing circuitry) 1505, and further includes a communicator (e.g., including communication circuitry) 1503 for communication with the biometric signal receiving and decompressing apparatus 11. In addition, the electronic apparatus 1 may further include a power supply (or a power management IC (not shown)) for managing power to be supplied to the electronic apparatus 1. The power supply may include a battery (not shown). The power supply (not shown) may use a wired and/or wireless charging method. The electronic apparatus 1 can determine a residue of the battery (not shown) or power consumption in the battery shown).

The measurer 1500 may include various measuring circuitry that measures a biometric signal of a person to be examined and generates the measured signal. As described above, the measurer 1500 may be differently configured in accordance with the kinds of biometric signal to be measured.

The signal processor 1501 may include various processing circuitry and serves to process the measured signal generated in the measurer 1500. The signal processor 1501 extracts the characteristic information from the waveform of the measured signal, and compresses the measured signal. The points for the medical diagnosis and the compression method may be differently applied in accordance with the kinds of measured biometric signal. Further, the measured signal generated by measuring the biometric signal in the measurer 1500 has periodicity corresponding to the characteristic of the biometric signal, and thus the signal processor 1501 is configured to extract a plurality of one-period signals corresponding to a plurality of periods, generate the characteristic information from each one-period signal and compress each one-period signal in order to compress the signal as described above. Further, the signal processor 1501 may be configured to use a template, of which difference from the extracted one-period signal is not higher than the threshold point, in compressing the one-period signal.

The communicator 1503 may include various communication circuitry and is configured to provide the extracted characteristic information and the compressed signal to the biometric signal decompressing apparatus 11. The communicator 1503 may send the extracted characteristic information and the compressed signal to the biometric signal decompressing apparatus 11 continuously, per preset period (e.g. 0.1 seconds, 0.5 seconds, 1 seconds or the like) or randomly.

The communicator 1503 is configured to remotely communicate with the biometric signal decompressing apparatus 11 directly or via a network or the like. The communicator 1503 is configured to provide information by a wired local area network (LAN) or wireless communication. In case of the wireless communication, the communicator 1503 may include various communication circuitry, such as, for example, and without limitation, a radio frequency (RF) circuit for transmitting and receiving an RF signal. The communicator 1503 may perform the wireless communication through a wireless LAN, Wireless Fidelity (Wi-Fi) or the like method. In addition, the communicator 1503 may perform the wireless communication with an external apparatus or network by Bluetooth or the like method.

In this example embodiment, the communicator 1503 may be configured to send the measured signal generated in the measurer 1500 and compressed in the signal processor 1501 to a hospital (e.g. a hospital server (not shown) or a hospital computer (not shown) corresponding to the biometric signal decompressing apparatus 11) through the network.

The communicator 1503 may be configured to send the measured signal generated in the measurer 1500 and compressed and encrypted in the signal processor 1501 to a hospital (e.g. a hospital server (not shown) or a hospital computer (not shown) corresponding to the biometric signal decompressing apparatus 11) through the network. The encryption of the compressed characteristic information and the compressed signal may include symmetric encryption or asymmetric encryption. The foregoing encryption is just given by way of example, and there are no limits to the encryption.

The biometric signal decompressing apparatus 11 receives the compressed characteristic information and the compressed signal. Further, if it is determined that a user has an emergency problem of health, the communicator 1503 may track his/her location and the measured signal may be allowed to be sent to various devices.

The controller 1505 may include various processing circuitry and is configured to control general operations of the biometric signal measuring apparatus 10. More specifically, the controller 1505 controls the measurer 1500 to measure a person to be examined in accordance with the kinds of biometric signal selected by a user and generate the measured signal having the waveform corresponding to the characteristic of the measured biometric signal, controls the signal processor 1501 to generate the characteristic information related to at least one medical diagnosis point included in the waveform of the measured signal and compress the measured signal, and controls the communicator 1503 to send the compressed signal and the characteristic information to the biometric signal decompressing apparatus 11. The controller 1505 may be configured to check the residue of the battery (not shown) or the like through the power supply (or the power management IC, not shown) for managing the power to be supplied to the electronic apparatus 1.

If the residue of the battery (not shown) of the electronic apparatus is 15% (where, 15% is just given by way of example and modifiable) of the total capacity of the battery, the controller 1505 may change the period of sending the extracted characteristic information and the compressed signal to the biometric signal decompressing apparatus 11. For instance, if the residue of the battery (not shown) of the electronic apparatus is sufficient (e.g. not lower than 16%), the controller 1505 may control the communicator 1503 to send the extracted characteristic information and the compressed signal to the biometric signal decompressing apparatus 11 per preset period (e.g. 1 second). On the other hand, if the residue of the battery (not shown) of the electronic apparatus is insufficient (e.g. not higher than 15%), the controller 1505 may change the period (e.g. 5 seconds or the like, which is just given by way of example) of sending the extracted characteristic information and the compressed signal to the biometric signal decompressing apparatus 11. In addition, the controller 1505 may restore the changed sending period of the communicator 1503 to its original period when the battery (not shown) of the electronic apparatus 1 is being charged.

As described above, the controller 1505 and the signal processor 1501 may be integrated into a single chip instead of separate individual elements.

Figure 16:
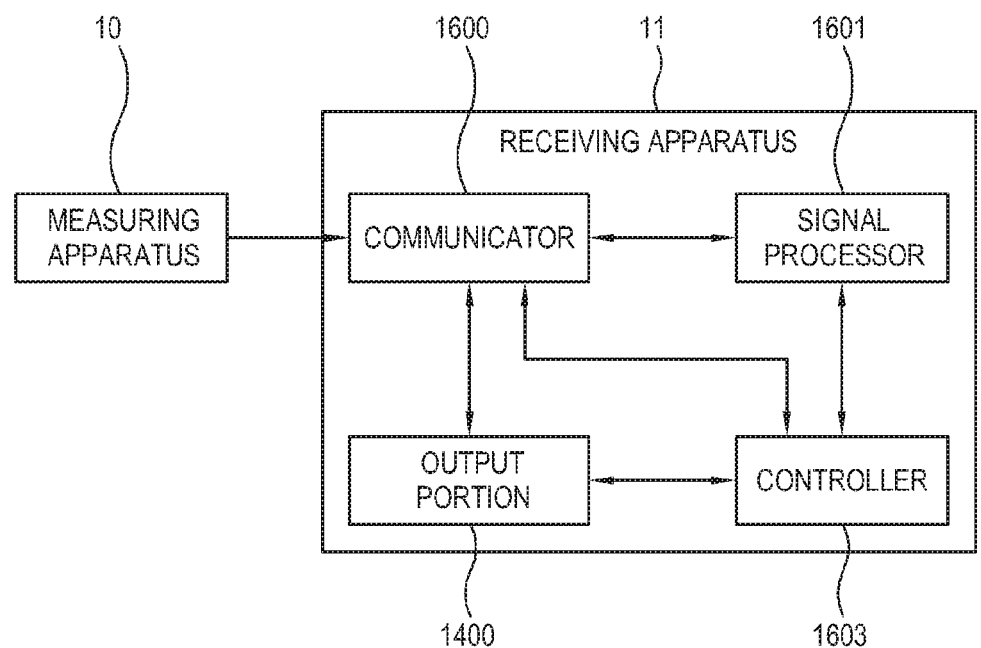
FIG. 16 is a block diagram illustrating an example apparatus for decompressing the biometric signal according to an example embodiment.

FIG. 16 is a block diagram illustrating an example biometric signal decompressing apparatus according to another example embodiment. The biometric signal decompressing apparatus 11 is also configured to include some elements of the foregoing electronic apparatus 1. For example, the biometric signal decompressing apparatus 11 includes a decompressor 1601, an output portion (e.g., including output circuitry) 1400 and a controller (e.g., including processing circuitry) 1603, and further includes a communicator (e.g., including communication circuitry) 1600 for communication with the biometric signal measuring apparatus 10.

The communicator 1600 may include various communication circuitry and is configured to receive the characteristic information and the compressed signal from the biometric signal measuring apparatus 10 by a wired or wireless communication.

The decompressor 1601 may include various circuitry and is configured to decompress the measured signal by a decompression method corresponding to the compression method. Information about the compression method may be offered to the biometric signal decompressing apparatus 11 as it is embedded in the compressed signal. The decompressor 1601 may select the decompression method based on the information about the compression method embedded in the compressed signal.

Further, as described above, the decompressor 1601 according to an example embodiment may be configured to restore the lost point based on previously extracted characteristic information if the medical diagnosis point to be used for the medical diagnosis is lost in the waveform of the measured biometric signal as the measured signal is compressed by the lossy compression.

The decompressor 1601 decompresses the compressed signal, compares the decompressed signal and the characteristic information, determines difference between the decompressed signal and the characteristic information as a loss, and restores the loss based on the characteristic information, thereby decompressing the compressed signal.

Further, if a previously stored template was used for compressing the signal, the decompressor 1601 according to an example embodiment may not decompress the compressed signal but apply the characteristic information embedded in the compressed signal to the template in order to decompress the compressed signal. The output portion 1400 may include various output circuitry and is configured to offer various pieces of information such as characteristic information, diagnostic information, a decompressed signal, etc. to a user. The output portion 1400 may include one of a display for displaying an image and a loudspeaker for making a sound.

The controller 1603 may include various processing circuitry and is configured to control general operations of the biometric signal decompressing apparatus 11. Specifically, if the compressed signal and the characteristic information are received from the biometric signal measuring apparatus 10, the controller 1603 controls the decompressor 1601 to analyze the kind of measured biometric signal, restore a loss of the compressed signal based on the characteristic information in accordance with the kind of biometric signal, and decompress the compressed signal. The controller 1603 may be also configured to provide the decompressed signal and the characteristic information to the output portion 1400 in response to a user's selection.

As described above, the decompressor 1601 and the controller 1603 may be provided as not individual elements but a single chip.

In this example embodiment, the controller 1603, which corresponds to a hospital (e.g. a hospital server (not shown) or a hospital computer (not shown)) of the biometric signal decompressing apparatus 11, controls the decompressor 1601 to decompress the compressed signal and the characteristic information received from the biometric signal measuring apparatus 10. In this example embodiment, the controller 1603, which corresponds to a hospital (e.g. a hospital server (not shown) or a hospital computer (not shown)) of the biometric signal decompressing apparatus 11, decrypts the encrypted compressed signal and characteristic information received from the biometric signal measuring apparatus 10.

Further, the biometric signal decompressing apparatus 11 further include a storage which stores health information for medical diagnosis of a person to be examined, analyzes health of a person to be examined (e.g. a user) through comparison between the characteristic information and the stored health information, generates diagnostic information, and provides the diagnostic information through the output portion 1400.

Figure 17:
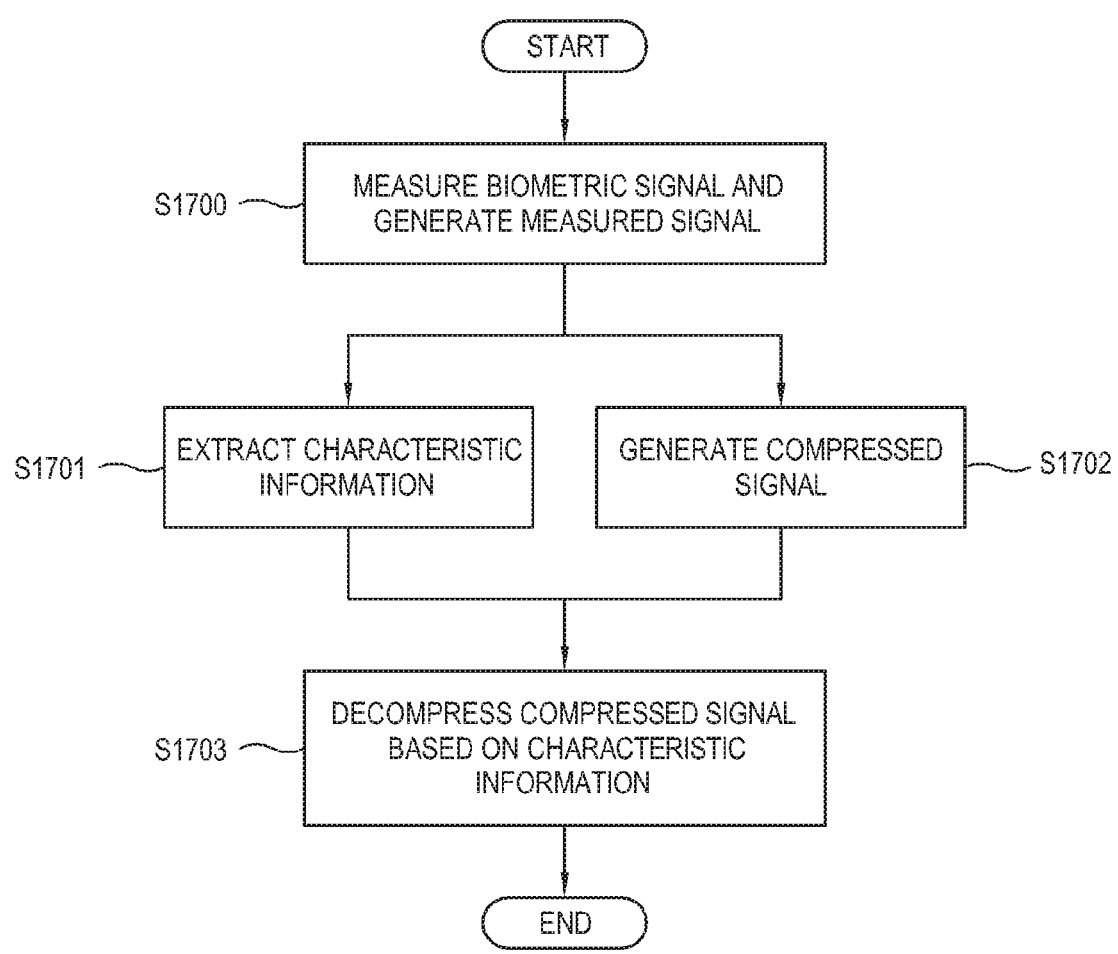
FIG. 17 is a flowchart illustrating an example method of controlling the electronic apparatus according to an example embodiment.

FIG. 17 is a flowchart illustrating an example method of controlling a medical apparatus according to an example embodiment. At operation S1700, the measurer 100 measures a biometric signal of a person to be examined with respect to the kind of biometric signal to be measured, and generates a measured signal having a waveform corresponding to a characteristic of a biometric signal. At operation S1701, the signal processor 200 generates at least one piece of characteristic information included in the waveform of the measured signal. At operation S1702, the signal processor 200 compresses the measured signal to thereby generate the compressed signal. At operation S1703, the decompressor 201 restores at least a part, which was lost in compressing the measured signal, based on the characteristic information, thereby decompressing the compressed signal.

The measured signal having the characteristic of the biometric signal has periodicity as described above. Under control of the controller 203, the signal processor 200 extracts a plurality of one-period signals respectively corresponding to a plurality of periods, generates the characteristic information from each waveform of the plurality of extracted one-period signals, and compress each one-period signal, in order to compress the measured signal having the periodicity (S1702). As described above, the previously stored template, of which difference from each one-period signal is not higher than the threshold point, may be used in order to compress each one-period signal.

In order to decompress the compressed signal (S1703), the decompressor 201 may apply the decompression method corresponding to the compression method, information of which is embedded in the compressed signal, to the plurality of compressed one-period signals under control of the controller 203. If the temperate was used for each one-period signal in order to compress the decompressor 201, the decompression may be achieved by applying the characteristic information to the used template as described above.

According to another example embodiment, the electronic apparatus 1 may output at least one of the decompressed signal and the characteristic information through the output portion 1100 in accordance with a user's selection. Further, the decompressor 201 may be configured to use the characteristic information changed in accordance with a user's selection while decompressing the compressed signal.

Since the signal processor 200 and the decompressor 201 can be integrated into a single chip, the signal processor 200 may be also configured to decompress the compressed signal based on the characteristic information.

Figure 18:
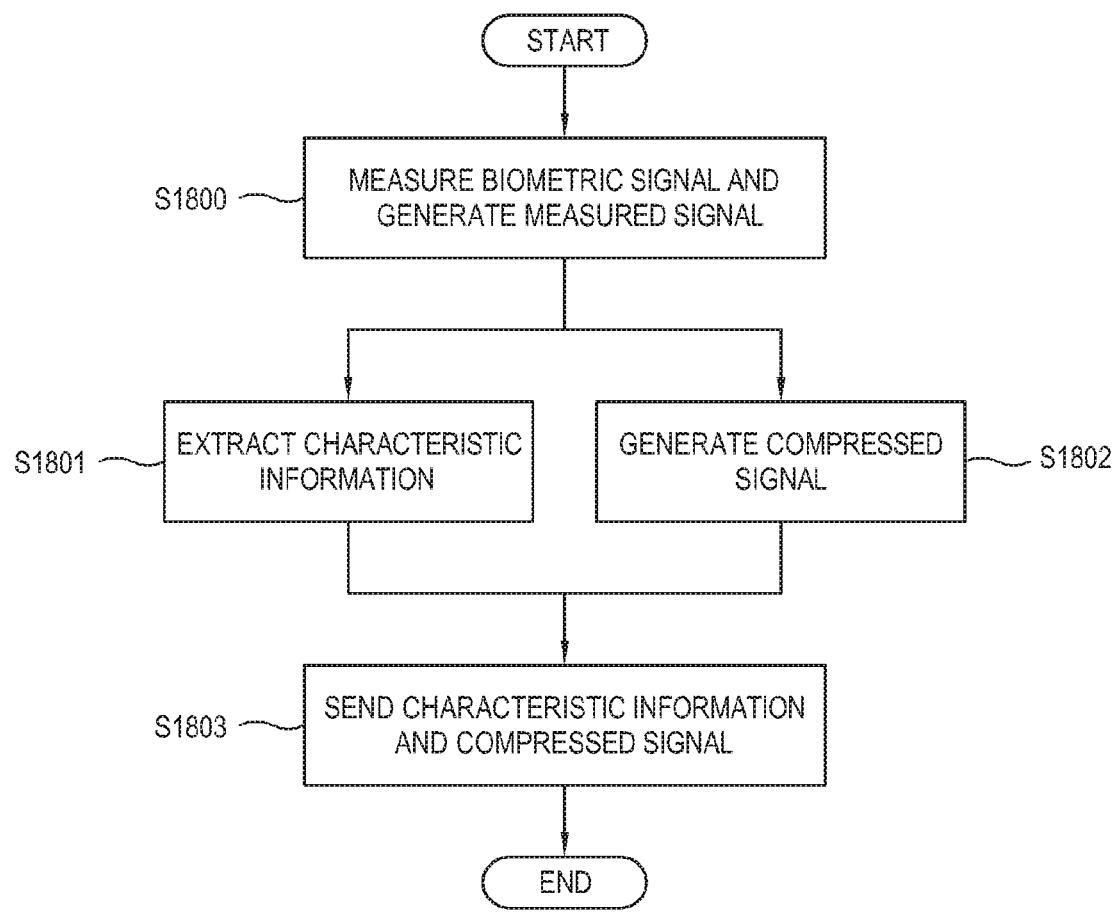
FIG. 18 is a flowchart illustrating an example method of controlling the apparatus for measuring a biometric signal according to an example embodiment.

FIG. 18 is a flowchart illustrating an example method of controlling the biometric signal measuring apparatus according to an example embodiment. At operation S1800, the measurer 1500 measures a biometric signal of a person to be examined with respect to the kind of biometric signal to be measured, and generates a measured signal having a waveform corresponding to a characteristic of the biometric signal. The signal processor 1501 extracts at least one piece of characteristic information from the waveform of the measured signal at operation S1801, and generates the compressed signal by compressing the measured signal at operation S1802. At operation S1803, the communicator 1503 sends the characteristic information and the compressed signal to the biometric signal decompressing apparatus 11.

In this manner, the biometric signal measuring apparatus 10 is provided separately from the biometric signal decompressing apparatus 11, measures a user's biometric signal, generates the characteristic information, compresses the measured signal and sends the compressed signal to the biometric signal decompressing apparatus 11. Before sending a signal, information is maximally compressed in order to efficiently use a frequency band for sending the signal and then sent, and the characteristic information is separately extracted and sent together with the compressed signal. According to another example embodiment, the compressed signal may be sent together with information about the compression method. If the template, of which difference from each one-period signal is not higher than the threshold point, is used in the compression, information about the used template or the like may be embedded in the compressed signal.

The biometric signal measuring apparatus 10 is configured to receive information about the kind of biometric signal from a user before measuring a biometric signal of a person to be examined, generate the measured signal based on the kind of selected biometric signal, extract the characteristic information, and compress the measured signal.

For the compression of the measured signal having the periodicity, the plurality of one-period signals respectively corresponding to the plurality of periods of the measured signal is extracted, and the characteristic information is generated from each one-period signal.

Figure 19:
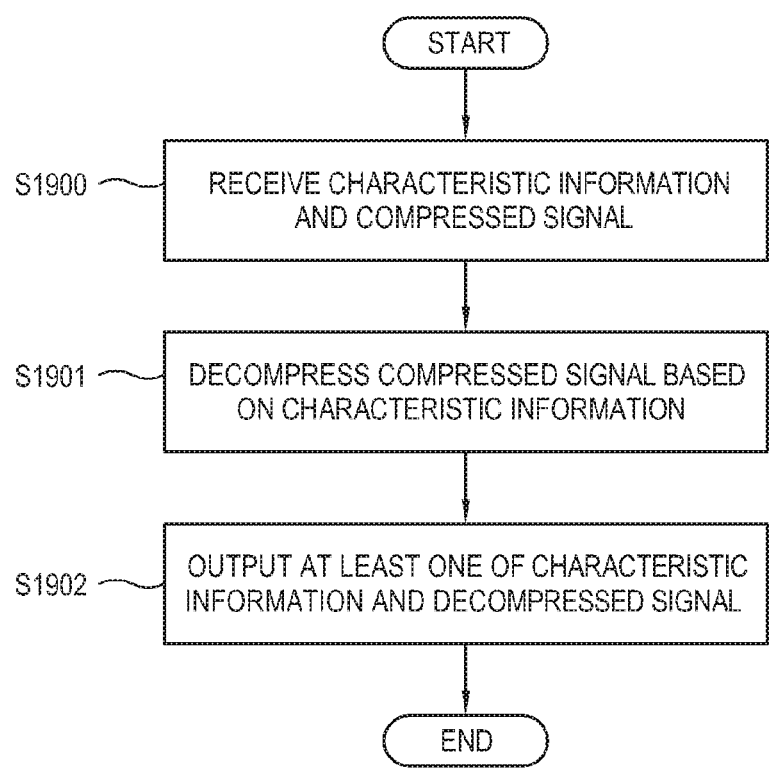
FIG. 19 is a flowchart illustrating an example method of controlling the apparatus for decompressing the biometric signal according to an example embodiment.

FIG. 19 is a flowchart illustrating an example method of controlling the biometric signal decompressing apparatus according to an example embodiment. At operation S1900, the communicator 1600 receives the characteristic information and the compressed signal from the biometric signal measuring apparatus 10. At operation S1901, the decompressor 1601 restores a part, which is lost in compressing the measured signal, based on the characteristic information, thereby decompressing the compressed signal. At operation S1902, the output portion 1400 outputs at least one of the characteristic information and the decompressed signal in accordance with a user's selection.

The biometric signal decompressing apparatus 11 may further include a user command input portion to receive a command for changing the characteristic information from a user. The decompressor 1601 may employ the changed characteristic information in restoring a part, which is lost in compressing the signal, of the signal, and the output portion 1400 may output the decompressed signal based on the changed characteristic information.

For the decompression of the compressed signal, the decompressor 1601 may compare each decompressed one-period signal and the characteristic information, determine difference between each decompressed one-period signal and the characteristic information as a loss, and restore the loss with respect to the characteristic information. The decompression may be achieved by a method corresponding to the compression method, and information about the compression method may be embedded in the compressed signal.

If the template was applied to each one-period signal in compressing the signal, the decompressor 1601 may decompress the compressed signal by applying the characteristic information to the used template.

The output portion 1400 includes various output circuitry, such as, for example, and without limitation, at least one of the display and the loudspeaker to offer information to a user.

The biometric signal decompressing apparatus 11 according to an example embodiment further includes the storage that stores health information for medical diagnosis of a person to be examined, thereby analyzing health of a person to be examined through comparison between the stored health information and the characteristic information, generating the diagnostic information, and providing the diagnostic information through the output portion 1400.

FIG. 20 is a diagram illustrating an example of extracting the one-period signals before compressing the biometric signal having the periodicity. The measured signal measured and generated by the measurer 100 has the periodicity since it has the characteristic of the biometric signal. For example, similar waveforms are repeated per specific period.

According to an example embodiment, the medical apparatus 1 extracts the plurality of one-period signals 2000 respectively corresponding to the plurality of periods in order to efficiently compress the biometric signal having the periodicity, generates the characteristic information from each extracted one-period signal 2000, and compress each one-period signal 2000.

FIG. 20 illustrates a process of extracting the plurality of one-period signals 2000 with respect to the R peak 305 by detecting the R peak 305 in the electrocardio graph (ECG). In the medical apparatus 1, the signal processor 200 generates various pieces of characteristic information such as positions of respective peaks 301, 303, 305, 307, 309 in the extracted one-period signal 2000 and intervals between the peaks 301, 303, 305, 307 and 309, selects a template, of which difference from the extracted one-period signal 2000 is not higher than the threshold point, and uses the selected template to compress each one-period signal 2000.

The process of compressing the one-period signal 2000 by the template is illustrate in FIG. 8.

FIG. 21 and FIG. 22 are diagrams illustrating examples of using an electronic apparatus according to example embodiments.

FIG. 21 illustrates an electronic apparatus 1 which is worn on a body part of a user and includes a measurer 100 placed on the bottom thereof so that a measured signal can be directly transmitted to a signal processor 200 or the like. Further, the electronic apparatus 1 decompresses a measured and compressed signal in accordance with a user's selection, and provides relevant information through a front display or the like.

FIG. 22 illustrates an electronic apparatus 1 wirelessly communicates with a measurer 100 to receive a measured signal. The electronic apparatus 1 may be achieved by a smart phone, a computer, etc. to compress the measured signal received from the measurer 100, generate characteristic information, decompresses the compressed measured signal, and provide information about at least one of the decompressed signal and the characteristic information to a user. The measurer 100 may be included in the electronic apparatus 1 as illustrated in FIG. 21, or may be placed outside the electronic apparatus 1 as illustrated in FIG. 22 and send the measured signal to the electronic apparatus 1.

As described above, according to an example embodiment, a biometric signal of a person to be examined is compressed and decompressed making a loss as little as possible, and then provided to a user.

Although various example embodiments have been illustrated and described, it will be understood by those skilled in the art that changes may be made in these example embodiments without departing from the principles and spirit of the disclosure, the scope of which is defined in the appended claims and their equivalents.

What is claimed is:

1. An electronic apparatus configured to measure a biometric signal, the electronic apparatus comprising:
   a measurer comprising measuring circuitry; and
   a processor configured to:

control the measurer to measure a biometric signal of a person to be examined, and to generate a measured signal having a waveform corresponding to a characteristic of the biometric signal;

process the generated measured signal; and generate both: (a) a compressed signal via lossy compression by compressing the measured signal in a manner so that biometric information is lost during the lossy compression, and (b) at least one piece of characteristic information included in a waveform of the measured signal, wherein the at least one piece of characteristic information comprises information configured for recovering at least a part of the biometric information of the measured signal lost by the lossy compression.

2. The electronic apparatus according to claim 1, wherein the processor is configured to decompress the compressed signal so that at least a part of the measured signal, which is lost by compression, can be recovered based on the characteristic information, when the compressed signal is decompressed.

3. The electronic apparatus according to claim 1, wherein the measured signal comprises a plurality of periods, and the processor is configured to generate a plurality of one-period signals by extracting a signal having one-period from the measured signal to correspond to each period of the measured signal, to generate the compressed signal by compressing each one-period signal, and to generate at least one piece of characteristic information included in each one-period signal.

4. The electronic apparatus according to claim 3, wherein the processor is configured to receive a selection based on a user input, to control the signal processor to generate the characteristic information from the measured signal based on a kind of biometric signal determined based on the received selection.

5. The electronic apparatus according to claim 1, wherein the biometric signal comprises at least one of: an electrocardio graph (ECG), a photoplethsymo graph (PPG), and a phonocardio graph (PCG).

6. The electronic apparatus according to claim 5, wherein the processor is configured to generate characteristic information related to at least one medical diagnosis point included in the waveform of the measured signal, and the medical diagnosis point comprises at least one of: a time when a plurality of peaks occurs in the waveform, an amplitude of each peak, intervals between the peaks, a difference in amplitude between the peaks, a period of the waveform, a position of a heart murmur in the waveform, and a level of the heart murmur.

7. The electronic apparatus according to claim 1, further comprising a storage configured to store health information, wherein the processor is configured to analyze the characteristic information based on the health information and to generate diagnostic information.

8. The electronic apparatus according to claim 7, wherein the processor is further configured to decompress the compressed signal, and further comprising an output portion comprising output circuitry configured to output at least one of the diagnostic information, the characteristic information and the decompressed signal.

9. The electronic apparatus according to claim 8, wherein the output circuitry comprises a display configured to display an image based on at least one of: the diagnostic information, the characteristic information and the decompressed signal.

10. The electronic apparatus according to claim 8, wherein the output circuitry comprises a loudspeaker configured to make a voice or sound based on at least one of: the diagnostic information, the characteristic information and the decompressed signal.

11. The electronic apparatus according to claim 1, wherein the processor is configured to receive a selection based on a user input, to change the characteristic information based on the received selection, and to decompress the compressed signal based on the changed characteristic information.

12. The electronic apparatus according to claim 1, wherein the processor controller is configured to generate a decompressed signal by decompressing the compressed signal, to compare the characteristic information and the decompressed signal, to determine a difference between the decompressed signal and the characteristic information as a loss, and to restore the loss based on the characteristic information to thereby decompress the compressed signal.

13. A method of controlling an electronic apparatus for measuring a biometric signal, the method comprising:

generating a measured signal having a waveform corresponding to a characteristic of the biometric signal by measuring the biometric signal of a person to be examined; and generating both: (a) a compressed signal by compressing the measured signal via lossy compression in a manner so that biometric information is lost during the lossy compression, and (b) characteristic information related to at least one medical diagnosis point included in the waveform of the measured signal, wherein the characteristic information comprises information configured to recover at least a part of the biometric information of the measured signal lost by the compressing via lossy compression.

14. The method according to claim 13, further comprising decompressing the compressed signal so that at least a part of the measured signal, which is lost by compression, can be recovered based on the characteristic information.

15. The method according to claim 13, wherein the measured signal comprises a plurality of periods, and the compressing the measured signal comprises:

generating a plurality of one-period signals by extracting a signal having one-period from the measured signal to correspond to each period of the measured signal; and generating the compressed signal by compressing each one-period signal, and generating at least one piece of characteristic information included in each one-period signal.

16. The method according to claim 13, wherein the biometric signal comprises at least one of: an electrocardio graph (ECG), a photoplethsymo graph (PPG), and a phonocardio graph (PCG).

17. The method according to claim 16, wherein the compressing the measured signal comprises: generating characteristic information related to at least one medical diagnosis point included in the waveform of the measured signal, and the medical diagnosis point comprises at least one of: a time when a plurality of peaks occurs in the waveform, an amplitude of each peak, intervals between the peaks, a difference in amplitude between the peaks, a period of the waveform, a position of a heart murmur in the waveform, and a level of the heart murmur.

18. The method according to claim 13, further comprising:

storing health information; and analyzing the characteristic information based on the health information and generating diagnostic information of a person to be examined.

19. The method according to claim 18, further comprising decompressing the compressed signal and outputting at least one of the health information, the diagnostic information, and the decompressed signal.

20. The method according to claim 13, further comprising decompressing the compressed signal, wherein the decompressing the compressed signal comprises:
  changing the characteristic information based on a received selection; and
  decompressing the compressed signal based on the changed characteristic information.

* * * * *